United States Patent [19]

Main et al.

[11] Patent Number: 5,533,661
[45] Date of Patent: Jul. 9, 1996

[54] SEALING MEANS FOR ENDOSCOPIC SURGICAL ANASTOMOSIS STAPLING INSTRUMENT

[75] Inventors: Lauren O. Main, Loveland; Richard L. Grant, Cincinnati, both of Ohio

[73] Assignee: Ethicon, Inc., Somerville, N.J.

[21] Appl. No.: 378,857

[22] Filed: Jan. 25, 1995

Related U.S. Application Data

[62] Division of Ser. No. 263,914, Jun. 22, 1994, abandoned, which is a division of Ser. No. 180,942, Jan. 12, 1994, Pat. No. 5,350,104, which is a continuation of Ser. No. 976,787, Nov. 16, 1992, Pat. No. 5,333,773, which is a continuation-in-part of Ser. No. 938,982, Sep. 1, 1992, Pat. No. 5,205,459, which is a division of Ser. No. 749,393, Aug. 23, 1991, abandoned.

[51] Int. Cl.$^6$ ................................................. A61B 17/068
[52] U.S. Cl. ........................ 227/176.1; 227/19; 227/179.1
[58] Field of Search ..................................... 227/175, 176, 227/179, 178, 180, 19

[56] References Cited

U.S. PATENT DOCUMENTS

| | | | |
|---|---|---|---|
| 5,084,057 | 1/1992 | Green et al. | 227/19 |
| 5,100,420 | 3/1992 | Green et al. | 227/19 |
| 5,170,925 | 12/1992 | Madden et al. | 227/19 |
| 5,193,731 | 3/1993 | Aranyi | 227/19 |

*Primary Examiner*—Scott A. Smith
*Attorney, Agent, or Firm*—Paul A. Coletti

[57] ABSTRACT

A sealed surgical stapling instrument for performing a circular anastomosis stapling operation is provided. The surgical instrument includes a stapling head assembly mounted by a curved shaft to an actuator handle assembly and incorporates an improved actuator mechanism for transmitting the required operating forces and movements from the actuator handle assembly through the curved shaft to an anvil and staple driver of the stapling head assembly. Various mechanisms for sealing the instrument are disclosed.

4 Claims, 26 Drawing Sheets

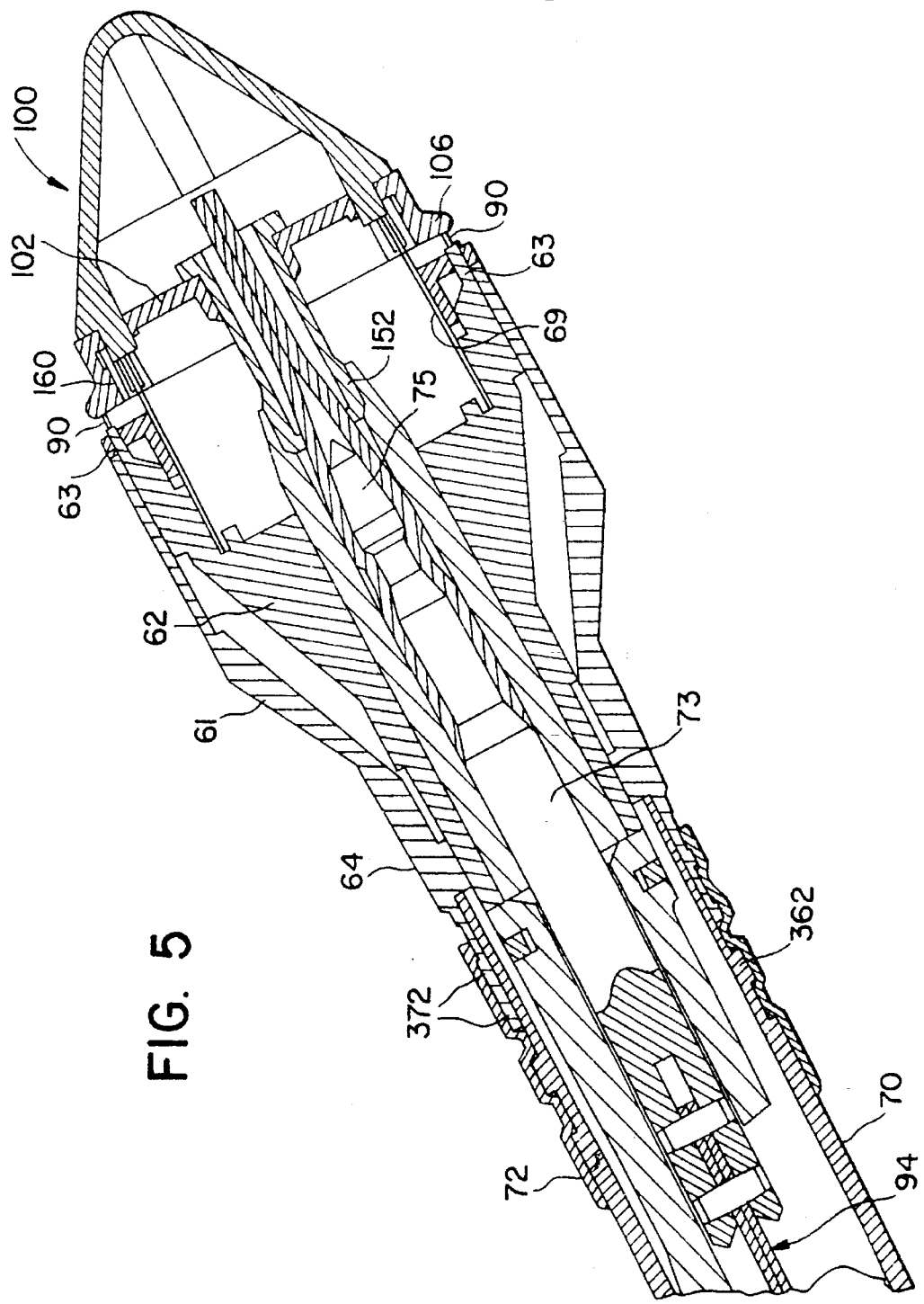

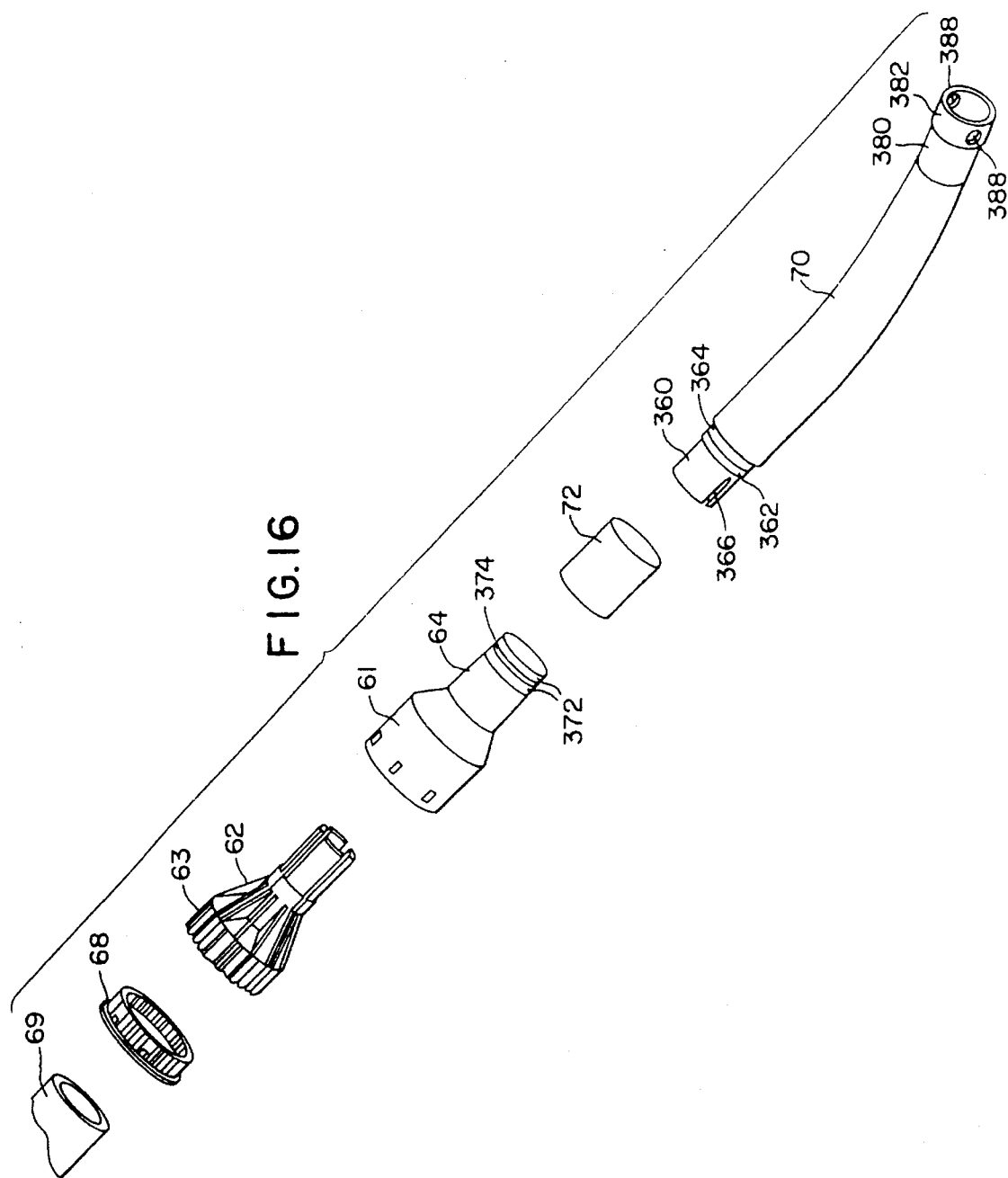

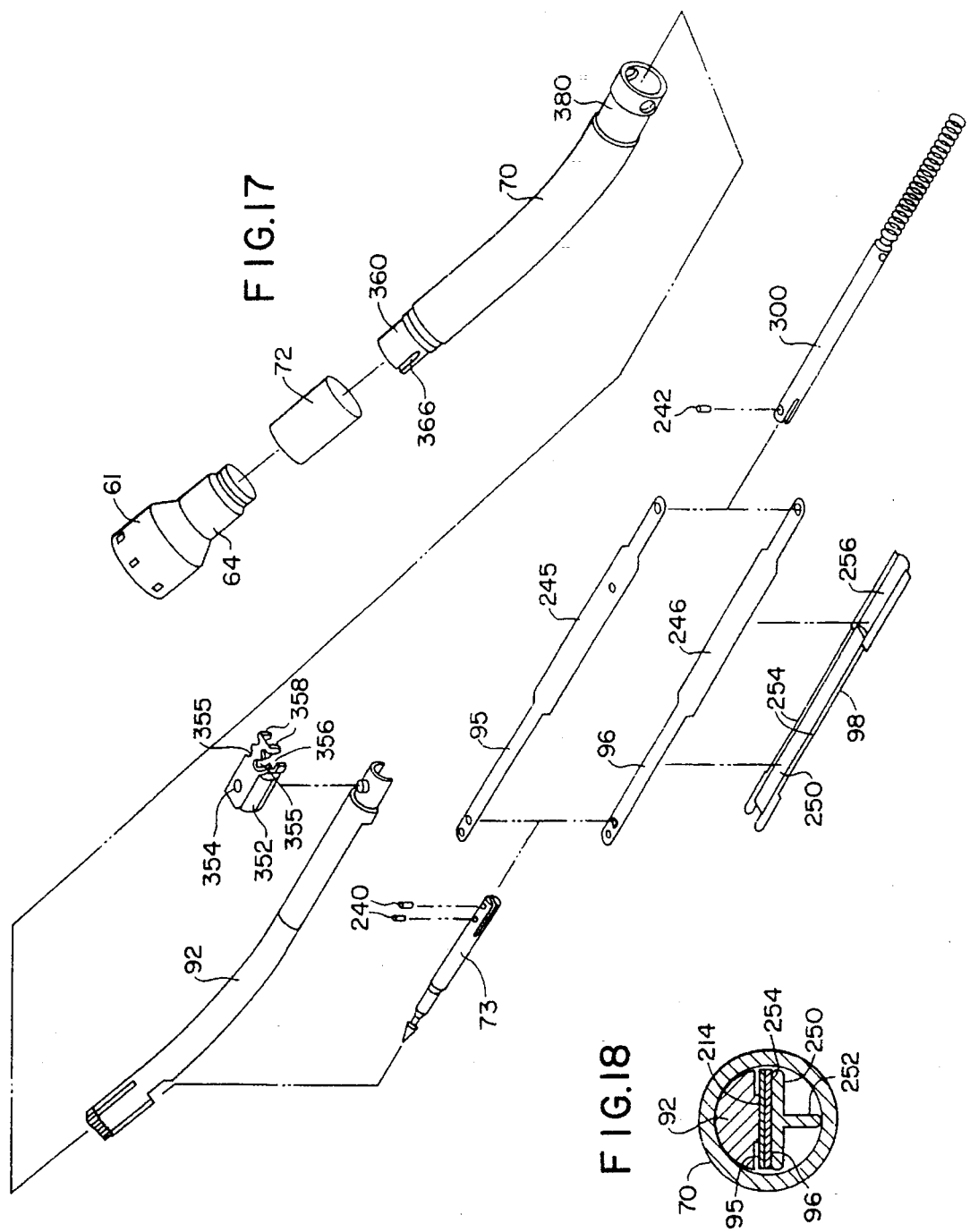

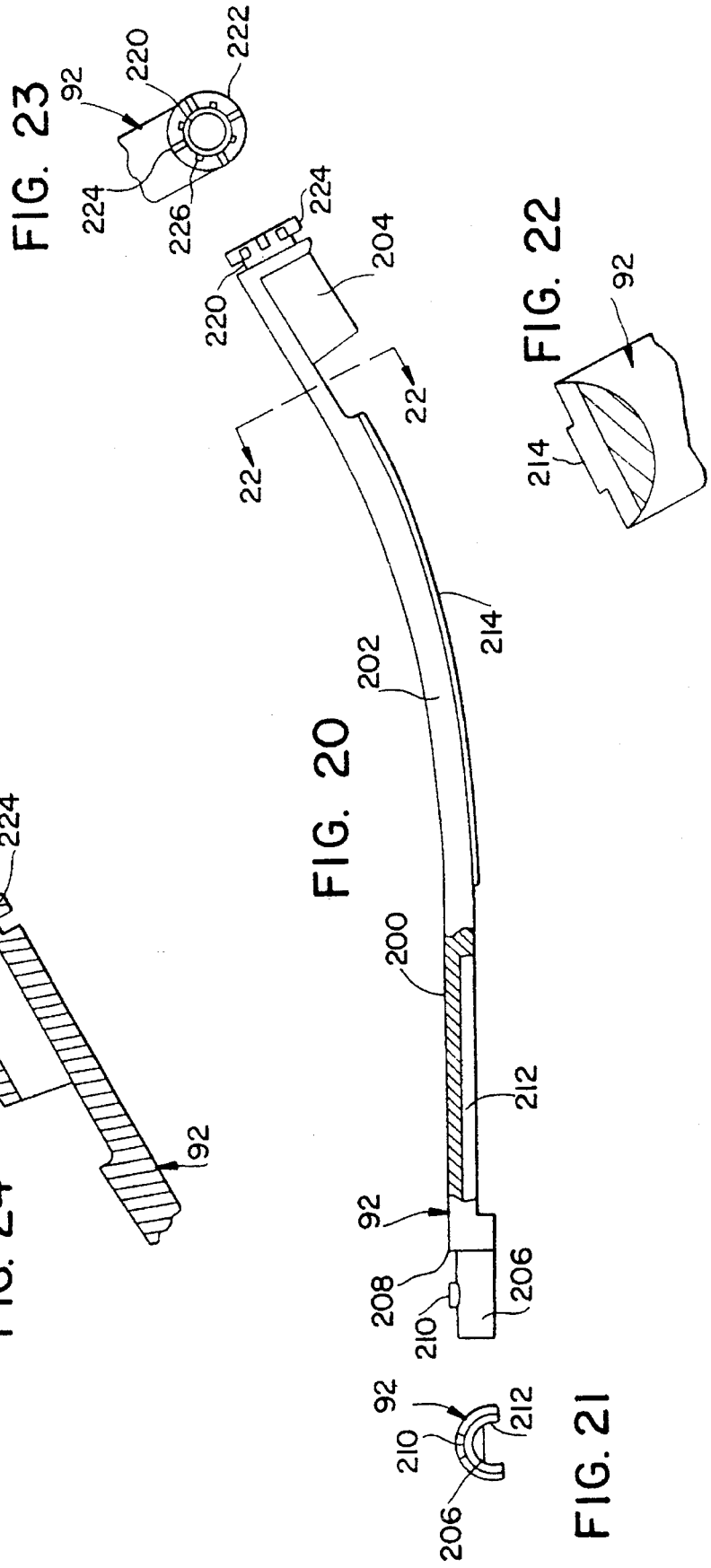

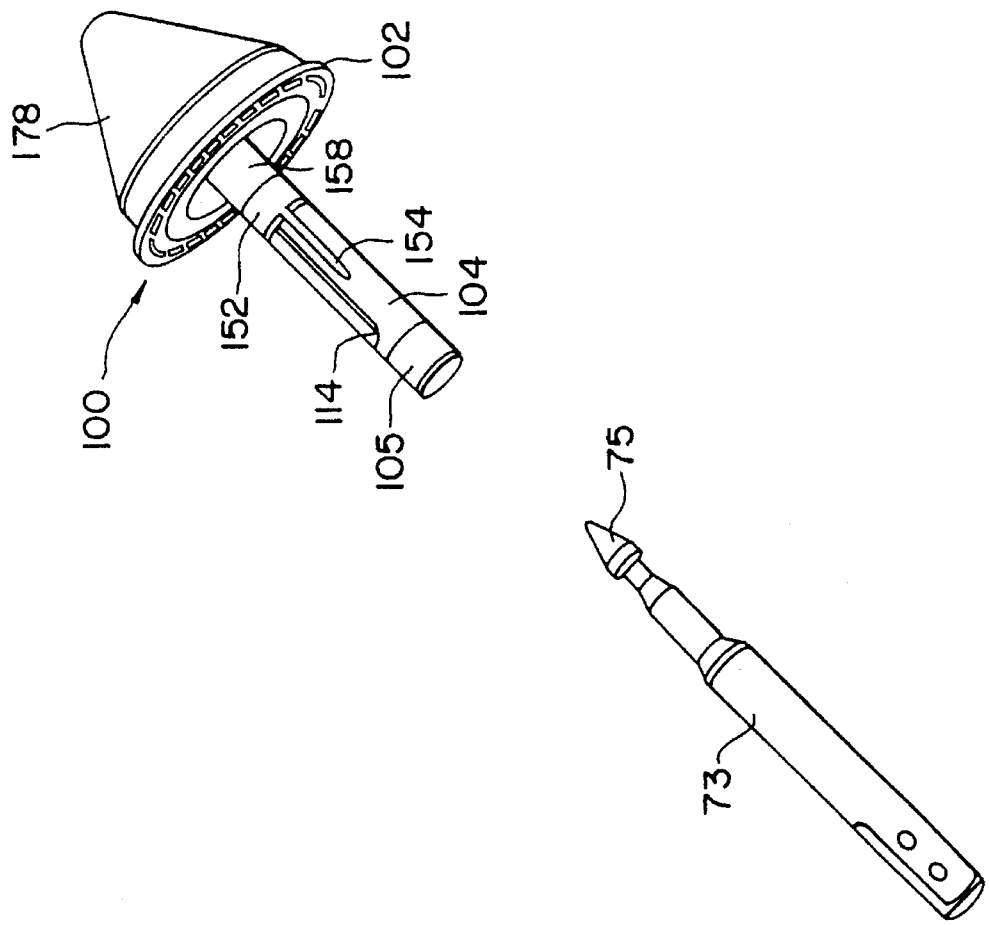

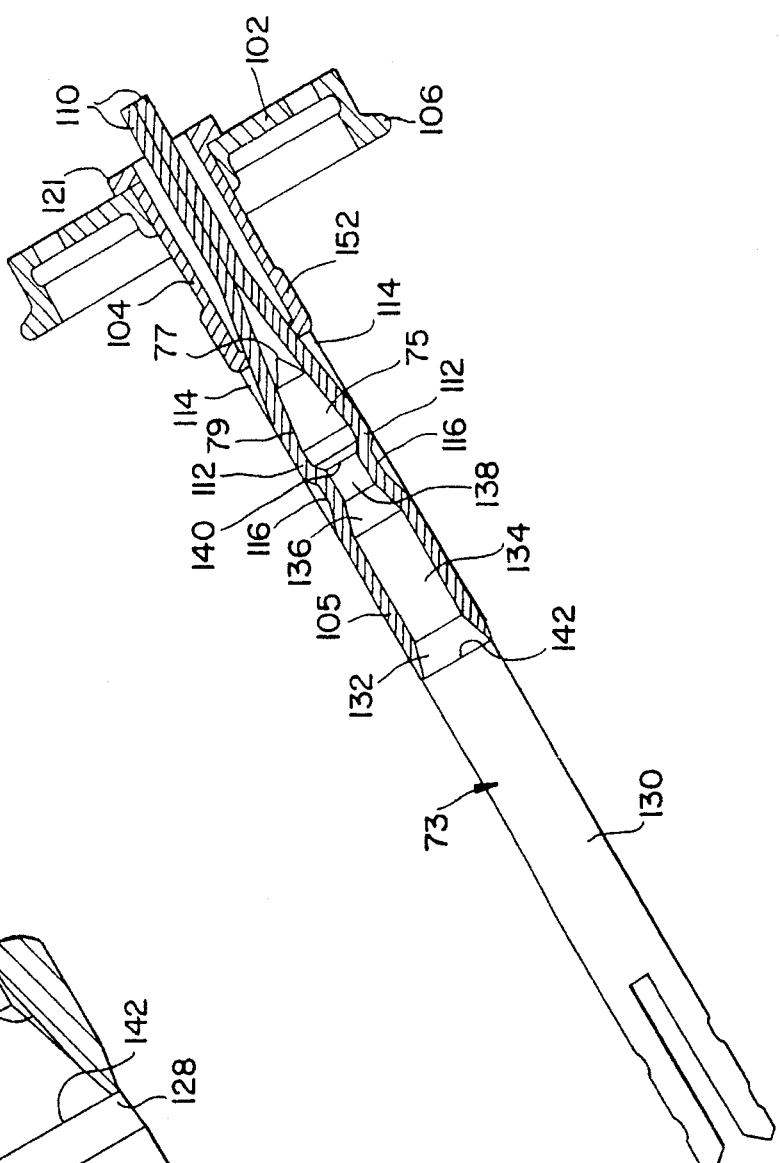
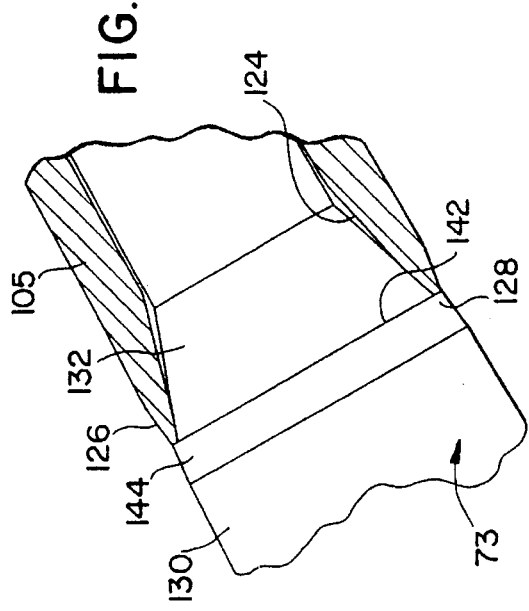

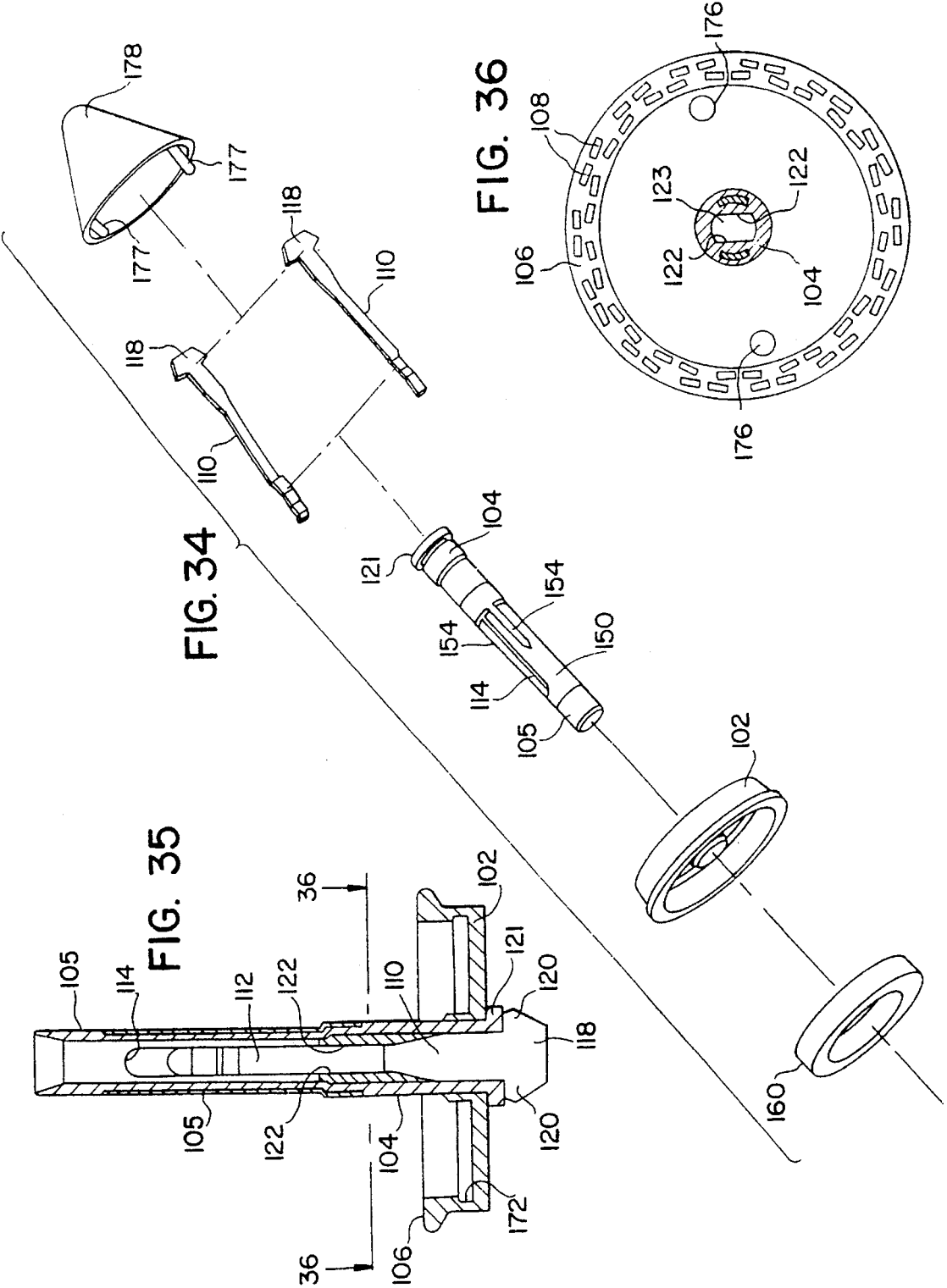

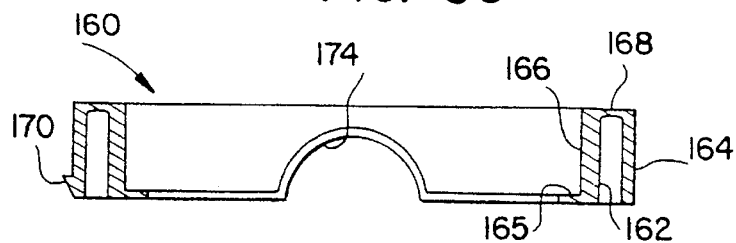
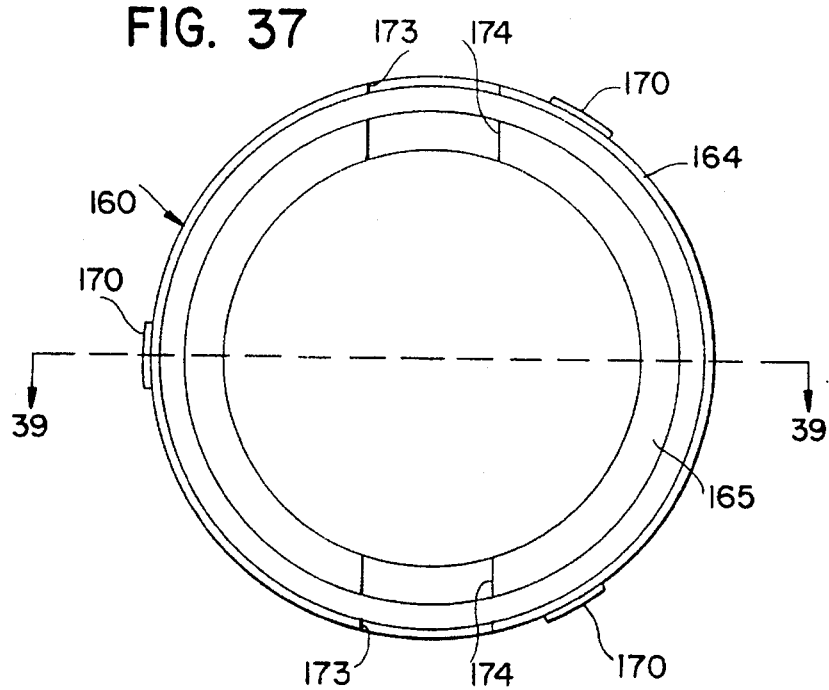
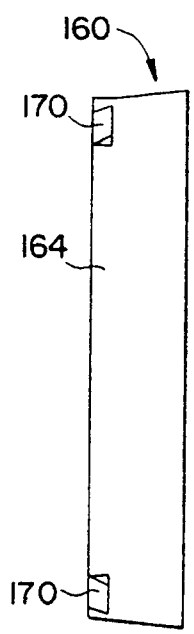

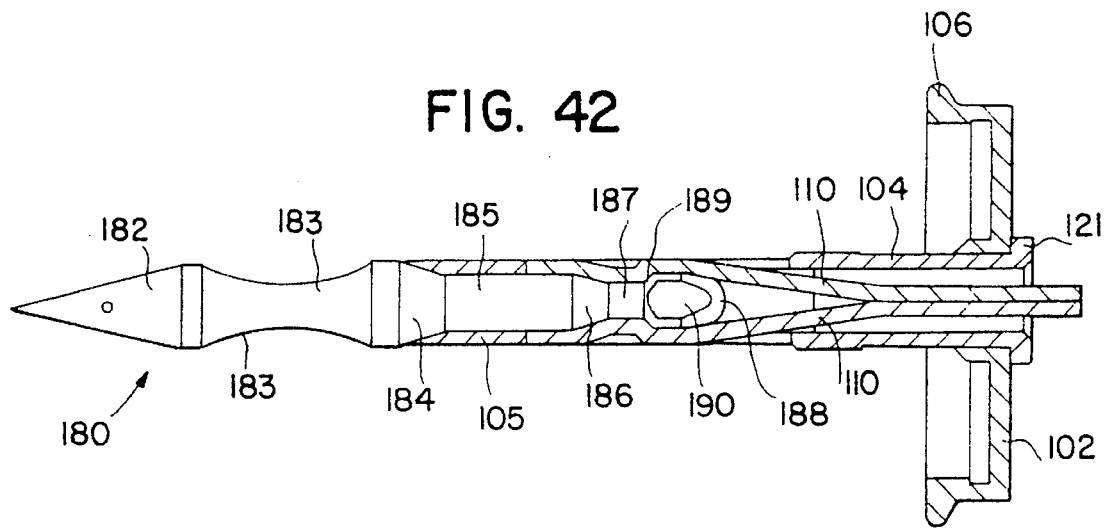
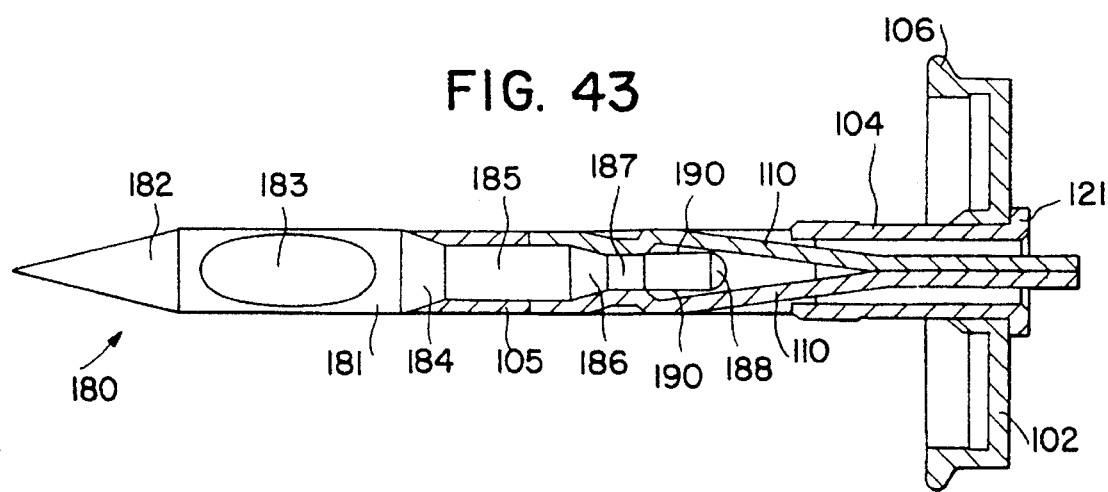

SEALING MEANS FOR ENDOSCOPIC SURGICAL ANASTOMOSIS STAPLING INSTRUMENT

This is a division of application Ser. No. 08/263,914 filed Jun. 22, 1994, abandoned, which is a division of Ser. No. 08/180,942, filed Jan. 12, 1994, now U.S. Pat. No. 5,350,104, which is a continuation of Ser. No. 07/976,787 filed Nov. 16, 1992, now U.S. Pat. No. 5,333,773, which is a continuation-in-part of Ser. No. 938,982 filed Sep. 1, 1992, now U.S. Pat. No. 5,205,459, which is a division of Ser. No. 749,393 filed Aug. 23, 1991, now abandoned.

FIELD OF THE INVENTION

The present invention generally relates to a surgical stapling instrument for applying surgical staples to tissue and, more particularly, to a surgical stapling instrument for performing a circular anastomosis stapling operation. More specifically, this invention relates to a surgical instrument in which a stapling head assembly is mounted by a curved shaft to an actuator handle assembly and to an improved actuator mechanism for transmitting the required operating forces and movements from the actuator handle assembly through the curved shaft to the stapling head assembly. Also, this invention relates to an improved stapling head assembly provided with a detachable anvil and a retractable staple driver. Further, this invention concerns an improved actuator mechanism which permits adjustment of the anvil gap to produce a desired staple height and precludes actuation of the stapling head assembly if the anvil gap is outside of a predetermined range.

BACKGROUND OF THE INVENTION

The field of surgical stapling has seen substantial advances in the past decades. Specifically, in the area of internal anastomotic stapling the advances have been quite dramatic. Devices such as the Proximate™ ILS stapler, produced by the assignee of the present invention, Ethicon, Inc., Somerville, N.J., have enabled surgeons to perform operations and procedures which were heretofore perceived as difficult, if not impossible, with relative ease.

Generally, in the performance of a surgical anastomotic stapling operation, two pieces of lumen or tubular tissue, e.g., intestinal tissue, are attached together by a ring of staples. The two pieces of tubular tissue may be attached end to end or one piece of tubular tissue may be attached laterally around an opening formed in the side of another piece of tubular tissue. In performing the anastomosis with a stapling instrument, the two pieces of tubular tissue are clamped together between an anvil provided with a circular array of staple forming grooves and a staple holder provided with a plurality of staple receiving slots arranged in a circular array in which the staples are received. A staple pusher is advanced to drive the staples into the tissue and form the staples against the anvil. Also, a circular knife is advanced to cut the excess tissue clamped between the anvil and the staple holder. As a result, a donut-shaped section of tissue is severed from each lumen and remains on the anvil shaft. The tubular tissue joined by the circular ring of staples is unclamped by advancing the anvil shaft distally to move the anvil away from the staple holder. The stapling instrument is removed by pulling the anvil through the circular opening between the pieces of tubular tissue attached by the ring of staples.

In the prior art, several types of circular anastomosis stapling instruments are known. For example, U.S. Pat. Nos. 4,576,167 and 4,646,745 to Noiles disclose a surgical stapler in which a stapling assembly is connected by an elongated shaft assembly having a longitudinally curved section to an actuator assembly. The shaft assembly includes an articulated hollow tube and a flexible band inside the tube, which are coaxial with a curved section of a hollow support shaft, for transmitting the compression and tension forces required to operate the stapling assembly. The hollow compression tube is concentric with the hollow support shaft. The flexible tension band is disposed in the interior of the hollow compression tube. Two elongated flexible spacer elements are mounted inside the compression tube above and below the flexible tension band to maintain the tension band substantially in the center of the curved compression tube. The compression tube and the tension band are mounted coaxial with respect to the curved sections of the support shaft.

It is also known in the prior art to provide a circular anastomosis stapling instrument including a flexible shaft which allows the stapling head to assume various orientations relative to the actuator assembly. Examples of circular stapling instruments with flexible shafts are disclosed in Noiles et al U.S. Pat. No. 4,473,077, Barker et al U.S. Pat. No. 4,754,909, and Shichman U.S. Pat. No. 4,488,523.

European Patent Application No. 293,123-A2 discloses a surgical anastomosis stapling apparatus including a stapling assembly comprising a tubular housing which supports an annular array of staples, a staple pusher mounted for movement between a retracted position within the housing and an extended position for expelling the annular array of staples, and a cylinder slidably mounted within the pusher assembly for selectively mounting either a trocar or an anvil assembly. The cylinder includes a central bore at its distal end for receiving a solid anvil shaft which is releasably held in the central bore by a detent formed on a spring member mounted at the distal end of the cylinder. The anvil shaft includes external longitudinal splines which engage internal splines provided within the housing for aligning the anvil shaft with the housing.

U.S. application Ser. No. 590,404, filed Sep. 28, 1990, by Main now U.S. Pat. No. 5,104,025 and assigned to Ethicon, Inc., discloses a surgical stapling device including an anvil portion which is detachable from a stapling head portion containing a trocar tip upon which the anvil is attached. The anvil portion contains an elongated sleeve with an opening through which the trocar tip is inserted. The anvil is provided with a locking clip which releasably engages an indentation or ridge provided on the trocar tip which allows the anvil to be separated from the trocar tip.

Further, it has been found that staplers of this type may be used very capably within larger diameter trocars, such as trocars having an external diameter between 18 mm and 33 mm or larger. This size allows the stapling head of the anastomotic instrument to be inserted within the trocar. Of course, as with any surgical procedure, it is important to maintain insufflation within the body cavity. This can be difficult where the internal components of the surgical stapler leak, especially in conjunction with a trocar having a 33 mm diameter. This size allows large volumes of air to pass within the trocar chamber. Their sealing is necessary in order to enable through a less invasive opening in the abdomen.

SUMMARY OF THE INVENTION

The present invention achieves an improved surgical stapling instrument for applying surgical fasteners, such as staples, to human tissue which is particularly suited for performing a circular anastomosis stapling operation. The stapling instrument comprises a shaft assembly including a longitudinally curved support shaft for mounting a stapling head assembly on an actuator handle assembly. The stapling head assembly includes a staple holder for receiving one or more surgical staples, an anvil for clamping the tissue against the staple holder, and driver means for engaging and driving the staples from the staple holder into the tissue and against the anvil. A tension member contained within the support shaft transmits tension from the actuator handle assembly to the anvil to resist the forces exerted on the anvil when the staples are formed. A compression member contained within the support shaft transmits a compressive force from the actuator handle assembly to advance the driver means and drive the staples from the staple holder into the tissue and to form the staples against the anvil.

In accordance with the invention, the compression member has an elongated wall section extending through the support shaft and including an integral guide surface thereon for engaging and supporting the tension member. In a preferred embodiment, both the tension member and the compression member are flexible relative to the support shaft. Preferably, the tension member comprises an elongated flexible band which is capable of flexing as it slides relative to the integral guide surface on the compression member. The compression member consists of material, e.g., fiber filled plastic material, which is flexible relative to the support shaft. In operation, the flexible tension band follows the curvature of the guide surface of the compression member. Since both are flexible, the tension band and the compression member change in curvature during movement relative to the curved support shaft which has a uniform radius of curvature between the stapling head assembly and the actuator assembly. Preferably, the elongated wall section of the compression member has a non-tubular cross section which is not concentric or coaxial with the tension member. As a result, the tension member is not surrounded by or disposed within the compression member.

In a preferred embodiment of the stapling instrument, the actuator handle assembly includes a first actuator for controlling the motion of the anvil and a second actuator for controlling the motion of the staple driver. The anvil is mounted on an anvil shaft slidably supported for movement relative to the stapling head assembly to allow the tissue to be clamped between the anvil and the staple holder. The shaft assembly includes a longitudinally curved tubular support shaft which contains the tension member and the compression member. The tension member transmits longitudinal tension and longitudinal motion relative to the support shaft from the first actuator to the anvil shaft to move the anvil toward the staple holder to clamp the tissue and resist the forces exerted on the anvil when the staples are driven through the tissue and formed against the anvil. The compression member transmits a longitudinal compressive force and longitudinal motion relative to the support shaft from the second actuator to the staple driver to advance the staple driver to drive the staples from the staple holder into the tissue and against the anvil.

According to another aspect of the invention, the stapling instrument includes an actuator mechanism adapted to advance the staple driver relative to the staple holder to form the staples against the anvil and to retract the staple driver after the staples are formed. In the preferred embodiment, the staple driver is coupled to the compression member for transmitting both distal and proximal movement from the compression member to the staple driver. This feature permits the staple driver to be retracted after firing of the stapling instrument. Thus, if a staple, tissue, or other debris attached to the patient becomes lodged between the staple driver and the staple holder, the staple driver can be retracted to release the attachment to the patient and reduce the potential for damage to the tissue when the instrument is removed from the patient.

In accordance with another aspect of the invention, the stapling instrument includes an actuator mechanism which permits adjustment of the anvil gap and precludes actuation of the stapling head assembly if the anvil gap is outside of a predetermined range. The actuator mechanism includes a first actuator for adjusting the gap between the anvil and the staple holder, a second actuator for actuating the staple driver, and latch means responsive to the first actuator to prevent operation of the second actuator when the gap between the anvil and staple holder is outside of the predetermined range.

In the preferred embodiment, the first actuator comprises an adjusting knob rotatably mounted on the actuator handle assembly for adjusting the anvil gap and the second actuator comprises a trigger arm pivotally mounted on the actuator handle assembly for actuating the staple driver. A safety latch comprising a pivot lever is pivotable from a latched position engaged with the trigger arm to an unlatched position disengaged therefrom. A safety release member is mounted for longitudinal movement along the actuator handle assembly by the first actuator from a first position engaged with the safety latch when the anvil gap is outside of the predetermined range to a second position disengaged from the safety latch when the anvil gap is within the predetermined range.

Preferably, a control rod is mounted for longitudinal movement on the actuator handle assembly and connected at its distal end to the tension member which, in turn, is connected to the anvil. The anvil gap adjusting knob is threadably connected to the proximal end of the control rod for moving the control rod longitudinally when the adjusting knob is rotated. The control rod supports a clip for engaging and displacing the safety release member when the anvil gap is within the predetermined range to disengage the safety latch. Preferably, the clip is adjustable in longitudinal position on the control rod for purposes of calibration. A staple height indicator is operable by the safety release member when the anvil gap is within a desired operating range to indicate the staple height to be produced when the stapling instrument is operated. The staple height indicator is visible through a window on the actuator handle assembly.

In accordance with another aspect of the invention, the stapling instrument includes an anvil which is detachably secured to a trocar attached to the tension member and slidably received in the stapling head assembly for longitudinal movement relative to the staple holder. Retainer means comprising one or more retainer clips is provided on the anvil shaft for engaging the trocar and transmitting tension from the trocar to the anvil. Each retainer clip extends distally through the anvil and has one or more lateral projections at its distal end for applying tension to a distal portion of the anvil. The retainer clips carry the tension forces from the tension member to the anvil and no tension load is applied to the anvil shaft. The retainer clips, which are biased opened by a trocar tip at the distal end of the trocar, capture the trocar tip when the trocar is fully inserted into the anvil shaft. The retainer clips permit the anvil shaft to be attached or detached by pushing or pulling, respectively, on the anvil while the stapling instrument is in the open position.

When the stapling instrument is closed, the anvil shaft is pulled into a central support tube which prevents the retainer clips from disengaging the trocar tip. With the stapling instrument in its firing position, the retainer clips are restrained by the support tube from disengaging the trocar tip to enable sufficient tension to be applied to the anvil to resist the full firing force of the stapling instrument. The retainer clips are located on the anvil shaft, not inside the stapling head assembly, so that the latching of the retainer clips to the trocar can be observed and audible feedback obtained as the retainer clips snap into place about the trocar tip.

In accordance with another aspect of the invention, the stapling instrument includes an improved system for aligning the anvil with the staple holder. A raised circumferential section on the anvil shaft is adapted to fit into the central support tube when the anvil shaft is retracted into the support tube to axially align the anvil with the staple holder. One or more external splines on the anvil cooperate with one or more internal splines on the central support tube to align the anvil rotationally with the staple holder. Preferably, the internal splines in the central support tube are spaced proximally away from the distal end of the support tube to provide an area for the raised circumferential section of the anvil shaft to interface with the central support tube. The internal splines have chisel points located below or proximal to the distal end of the central support tube to allow the tissue to slide over the external splines as the stapling instrument is closed, avoiding the potential of tissue, staples, and other debris becoming lodged between the splines. The raised circumferential section on the anvil shaft engages the central support tube to align the anvil shaft axially with the central support tube. The raised circumferential section on the anvil shaft fits tightly inside the central support tube to resist lateral forces and forces set up by imbalanced tissue loading between the anvil and the staple holder.

According to another aspect of the invention, an improved transition is provided between the trocar and anvil shaft to facilitate the transfer of tissue therebetween. The trocar has a small circumferential lip for engaging the proximal end of the sleeve when the trocar is inserted into the anvil shaft. The anvil shaft is chamfered at its proximal end to provide a thin circumferential edge for engaging the small circumferential lip on the trocar. The trocar is chamfered proximally of the circumferential lip to facilitate movement of the tissue along the trocar and onto the sleeve. Preferably, the thin circumferential edge of the sleeve has a slightly smaller diameter than the circumferential lip of the trocar. These features permit purse stringed tissue to slide over the transition between the trocar and the anvil shaft as the stapling instrument is closed without lodging tissue, staples, or other debris in the small gap between the trocar and the anvil shaft.

According to another feature of the invention, the central support tube is adapted to push the purse stringed tissue over the external splines to reduce the amount of tissue pulled into the stapling head assembly during closure of the stapling instrument. Preferably, the central support tube has a flat end located adjacent to the surface of the staple holder, rather than deep inside the stapling head assembly, to hold the purse stringed tissue near the surface of the staple holder rather than being pulled into the stapling head assembly. This feature reduces the total amount of tissue pulled into the stapling head assembly and cut off by the scalpel. By reducing the quantity of tissue pulled into the stapling head assembly, the risk of overloading is avoided and the stapling instrument does not trim excess viable tissue.

In accordance with another aspect of the invention, the anvil includes a backup member which cooperates with the scalpel to cut the tissue and which is secured to the anvil in a manner to prevent dislodgement in the shipping and handling of the stapling instrument. Preferably, an annular backup washer is mounted on the anvil adjacent to an inner annular groove formed therein. The washer includes securing means comprising a plurality of detents formed thereon and received in the annular groove to retain the washer on the anvil. This feature avoids the potential for accidental dislodgement of the backup washer associated with other stapling instruments which have utilized a frictional force fit between the anvil and the backup washer.

Another aspect of the invention resides in a low force trocar which reduces the amount of force required to insert the trocar between the retainer clips inside the anvil shaft. To reduce the force required to bias open the retainer clips, the trocar tip is tapered at a shallow angle permitting attachment of the anvil shaft to the trocar with an endoscopic grasper. For example, the trocar tip is made conical in shape with a taper of 30 degrees or less relative to the trocar axis to facilitate the insertion of the trocar tip between the retainer clips. In a preferred embodiment, the trocar tip has a conical nose at its distal end tapered at 30 degrees and an adjacent conical surface tapered at 9 degrees for biasing open said retainer clips when said trocar is inserted into said anvil shaft.

Another feature of the invention resides in a low force removable trocar which is compatible with endoscopic procedures. A removable trocar is provided for temporary attachment to the anvil shaft for piercing of tissue with the anvil assembly. The detachable trocar includes a trocar tip for engaging the retainer clips upon insertion of the trocar into the anvil shaft to hold the trocar between the retainer clips. The trocar tip includes one or more recesses which upon alignment with the retainer clips permit the detachable trocar to engage or disengage the retainer clips with a reduced force. Preferably, the trocar tip has a pair of opposed flat sides which, when aligned with the retainer clips, reduce the force required to insert or remove the trocar. The full strength of the retainer clips can be utilized by rotating the trocar to a position where the flat sides are not aligned with the retainer clips. This feature permits the attachment and detachment of the trocar when rotated to the low force position by using an endoscopic grasper. With the trocar rotated to the high force position, the potential of dislodging the trocar while the anvil is pulled through tissue is reduced.

A further aspect of the invention relates to an improved system of attaching the stapling head assembly to the support shaft of the stapling instrument. A ferrule is fitted over the support shaft and the casing and is shrunk over the joint therebetween by using a magnetic field or thermal treatment to produce a frictional or shear bond between the casing and the support shaft. Preferably, the ferrule is compressed radially inward over a hollow support shaft and a hollow connector on the casing which are adapted to telescope together. A key on the tubular connector is received by a slot on the support shaft for rotational alignment of the casing with the support shaft. Preferably, one or more circumferential collars on the support shaft and the connector provide a series of alternating ridges and depressions over which the ferrule is deformed to join the support shaft and the casing together. Another ferrule which is compressed radially inward by a magnetic deforming process or by thermal treatment is used to join the support shaft to the actuator handle assembly. This bonding method permits adjustment of the overall length and rotational alignment of the stapling instrument to compensate for tolerances of the various internal components of the stapling instrument.

In another embodiment of this invention, there is provided a triple sealing mechanism capable of sealing the instrument entirely in its longitudinal direction so that it may be emplaced within a large diameter trocar, of 18 mm to 33 mm, or greater. There is a distal seal which is comprised of a cylindrical silicone insert filled with silicone grease which fits around the external portion of the sliding mechanisms in the head of the device. There is an intermediate seal which is another silicone insert which seals internally around the tension bands used to accomplish stapling by this mechanism. There is provided a proximal seal, which is a shrink tube formed on the outside diameter of the mechanism. This shrink tube has a sealing quality after it has been shrunk around the shaft and had, perhaps, has had an application of lithium grease emplaced between the shaft and the shrink wrap. Finally, at the magneformed points on the shaft there may be provided O-rings underneath the tube, to further cause sealing of the entire mechanism.

BRIEF DESCRIPTION OF THE DRAWINGS

The foregoing and other objects, aspects and advantages will be better understood from the following detailed description of the preferred embodiments of the invention with reference to the drawings, in which:

FIG. 5 is an enlarged longitudinal section view of the stapling head assembly illustrating the staple driver in its fired position;

FIG. 6 is an enlarged fragmentary view of a staple being formed against the anvil;

FIG. 11 is a perspective view of a safety release member in its latched position;

FIG. 12 is a perspective view of the safety release member in its unlatched position;

FIG. 15 is an enlarged fragmentary view of an indicator window on top the actuator handle assembly;

FIG. 16 is an exploded perspective view of the stapling head assembly and support shaft of the stapling instrument;

FIG. 17 is an exploded perspective view illustrating the tension and compression members mounted within the support shaft of the stapling instrument;

FIG. 18 is a cross section view of the support shaft assembly taken along line 18—18 of FIG. 9;

FIG. 20 is a partially cutaway side view of a compression member of the shaft assembly;

FIG. 21 is a proximal end view of the compression member;

FIG. 22 is a section view of the compression member taken along line 22—22 of FIG. 20;

FIG. 23 is a distal end view of the compression member;

FIG. 24 is an enlarged partially cutaway longitudinal section view of the distal end of the compression member;

FIG. 31 is a perspective view of the anvil of the stapling instrument showing the anvil shaft detached from a trocar contained in the stapling head assembly;

FIG. 32 is an enlarged, partially cutaway side view showing the anvil shaft attached to the trocar;

FIG. 33 is an enlarged fragmentary view illustrating the interface between the anvil shaft and the trocar;

FIG. 34 is an exploded perspective view illustrating a pair of retainer clips and a backup washer included in the anvil assembly;

FIG. 35 is an enlarged longitudinal section view of the anvil assembly without the washer;

FIG. 36 is a section view of the anvil assembly with the retainer clips removed;

FIG. 37 is a bottom view of the backup washer of the anvil assembly;

FIG. 38 is a side view of the backup washer;

FIG. 39 is a section view of the backup washer taken along line 39—39 of FIG. 37;

FIG. 42 shows the detachable trocar inserted into the anvil shaft in a high force position;

FIG. 43 shows the detachable trocar inserted into the anvil shaft in a low force position;

DETAILED DESCRIPTION OF PREFERRED EMBODIMENTS

Figure 1:
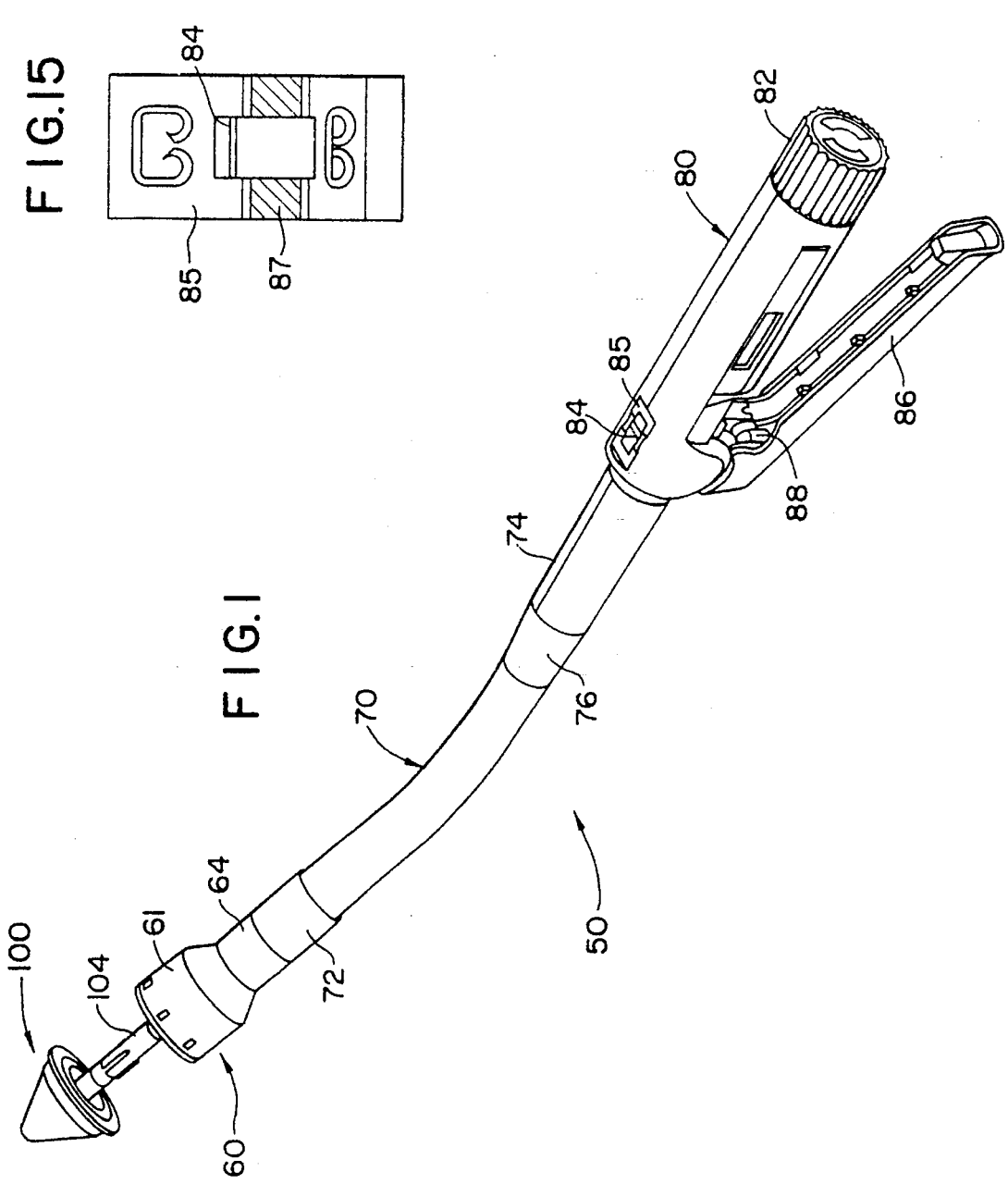
FIG. 1 is a perspective view of a surgical stapling instrument constructed in accordance with this invention illustrating a general overall view of the instrument.

Referring to FIG. 1, the present invention is embodied in a circular anastomosis surgical stapling instrument, generally 50, which includes a distal stapling head assembly 60 connected by a longitudinally curved support shaft assembly 70 to a proximal actuator handle assembly 80. The stapling instrument includes an anvil assembly 100 which is slidable longitudinally relative to the stapling head assembly 60. A rotatable adjusting knob 82 is provided at the proximal end of the actuator handle assembly 80 for adjusting the spacing between the stapling head assembly 60 and the anvil assembly 100. A movable indicator 84 is visible through a window 85 on top of the handle assembly 80 to indicate the staple height selected by rotation of the adjusting knob 82. As shown in FIG. 15, the indicator 84 is movable along a scale 87 which indicates that the anvil gap is within a desired operating range of the stapling instrument 50. The position of the indicator 84 also indicates whether the selected staple height is large or small.

A staple actuating lever 86 is pivotally mounted on the actuator handle assembly 80 for driving the surgical staples from the stapling head assembly 60 when the anvil assembly 100 is closed to provide the desired staple height. A pivotal latching member 88 is mounted on the handle assembly 80 for locking the staple actuating lever 86 against movement to preclude actuation of the stapling head assembly 60 when the anvil gap is outside of a predetermined range.

Figure 2:
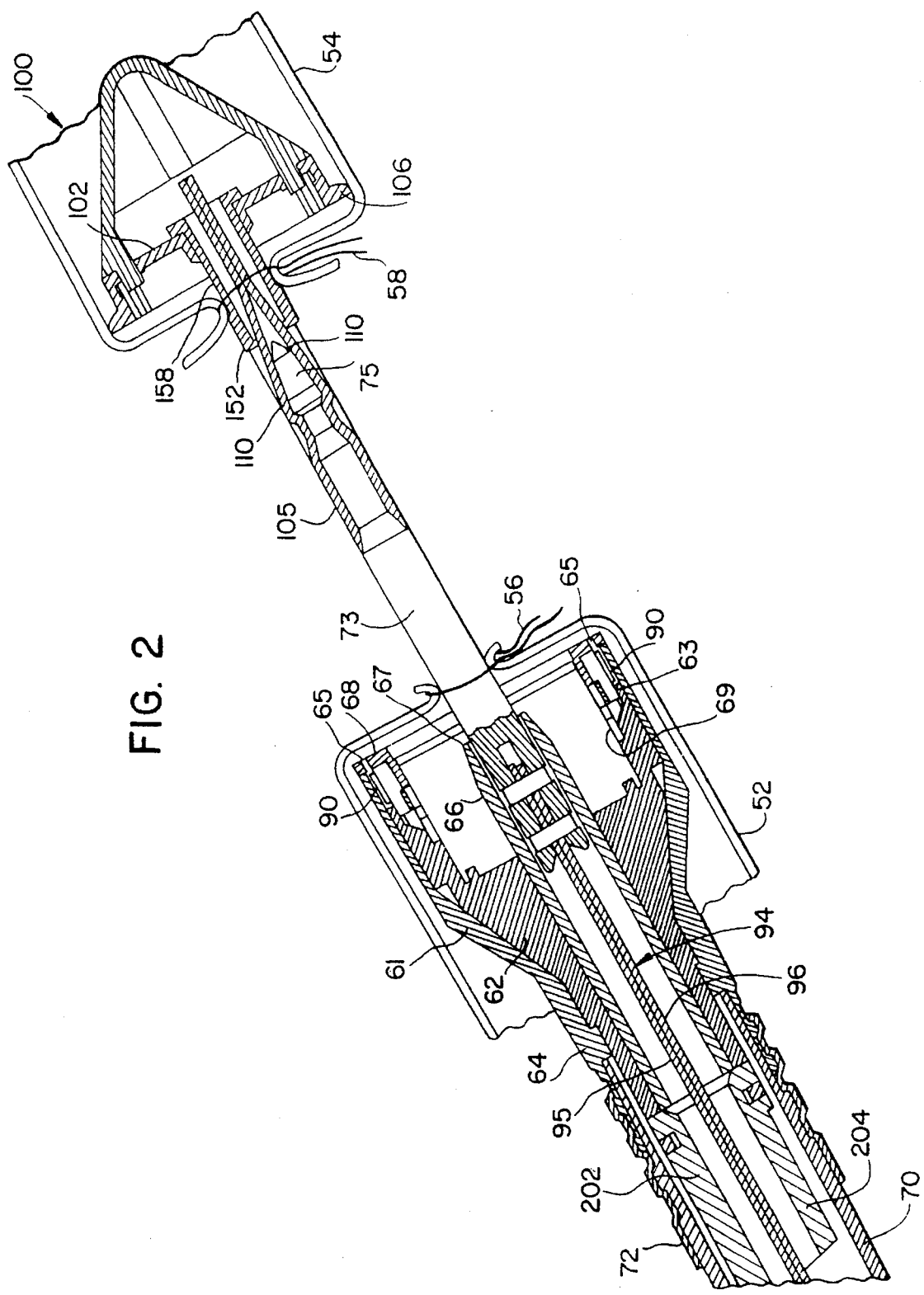
FIG. 2 is a longitudinal, vertical section view of a stapling head assembly of the instrument of FIG. 1 showing the anvil fully open.
Figure 3:
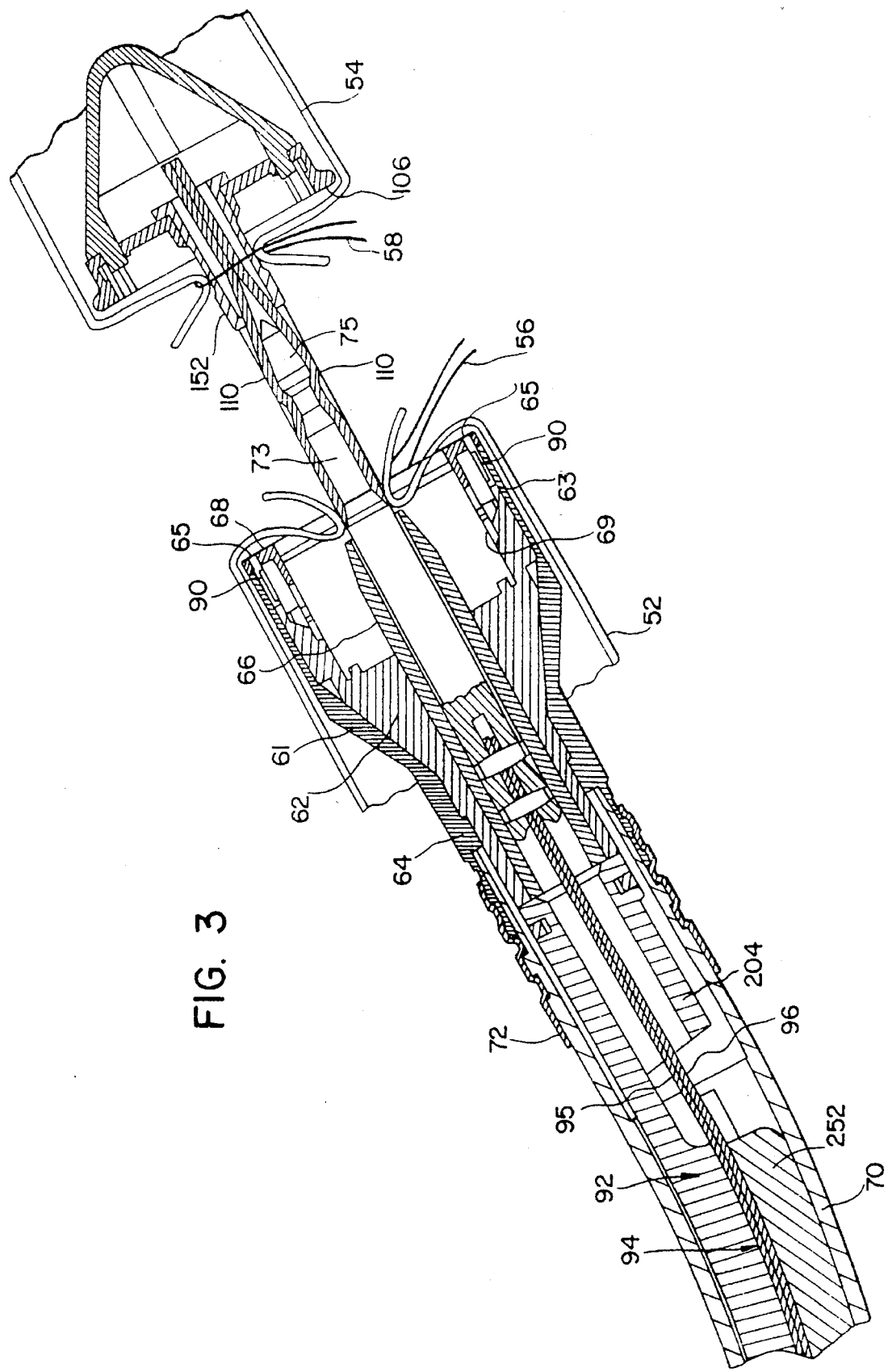
FIG. 3 is an enlarged longitudinal section view of the stapling head assembly illustrating the anvil in a partially closed position.

Referring to FIGS. 2 and 16, the stapling head assembly 60 includes a tubular casing 61 which slidably receives a staple driver 62 which can be advanced and retracted by operation of the actuator handle assembly 80. The staple driver 62 includes a plurality of fingers 63 for engaging and driving a plurality of staples 90 from a staple holder 68 mounted at the distal end of the casing 61. The staple holder 68 includes a plurality of staple receiving slots 65 into which the staples 90 are inserted. Also, the staple driver 62 supports a circular knife or scalpel 69 which is advanced and retracted with the staple driver 62.

The stapling head assembly 60 includes a hollow tubular connector 64 at the proximal end of the casing 61 which receives the distal end of the support shaft 70. A ferrule or sleeve 72 overlaps the joint between the tubular connector 64 and the distal end of the support shaft 70. The ferrule 72 is compressed or shrunk radially inward, e.g., by an electromagnetic deforming process, to securely fasten the tubular connector 64 to the distal end of the support shaft 70. Similarly, the proximal end of the support shaft 70 is received by a tubular extension 74 at the distal end of the actuator handle assembly 80. A ferrule or sleeve 76 overlaps the joint between the proximal end of the support shaft 70 and the distal end of the tubular extension 74. The ferrule 76 is compressed or shrunk radially inward, e.g., by a magnetic deforming process, to securely fasten the support shaft 70 to the actuator handle assembly 80.

Referring to FIGS. 2 and 31, the anvil assembly 100 includes a generally circular anvil 102 mounted on a hollow axially extending shaft 104 which is detachably secured to a trocar 73 slidably supported by the stapling head assembly 60. The trocar 73 includes a pointed trocar tip 75 which is inserted into a hollow sleeve 105 at the proximal end of the anvil shaft 104. The trocar 73 is slidably received within a central support tube 66 (FIG. 2) formed on the tubular casing 61 for longitudinal movement relative to the staple holder 68 mounted at the distal end of the casing 61. The staple receiving slots 65 in the staple holder 68 are arranged in a circular array for receiving the surgical staples 90. Preferably, the staple receiving slots 65 are arranged in two closely spaced concentric annular rows. The anvil 102 includes an annular rim 106 having a plurality of staple forming grooves 108 (FIG. 40) for forming the staples 90 when driven against the anvil 102.

The anvil assembly 100 includes a pair of elongated, spring-like retainer clips 110 extending longitudinally along the anvil shaft 104 for engaging the trocar tip 75 when the trocar 73 is inserted into the anvil shaft 104. As shown in FIG. 32, the retainer clips 110 extend longitudinally through anvil shaft 104 and include outwardly flared portions 112 which are received in longitudinal slots 114 disposed along opposite sides of the anvil shaft 104. The outwardly flared section 112 of each retainer clip 110 is bent radially inward to provide a detent 116 for capturing the trocar tip 75 therebetween. The elongated slots 114 permit the flared portions 112 of the retainer clips 110 to flex radially outward when the trocar tip 75 is inserted into the anvil shaft 104 and advanced between the detents 116.

To facilitate the insertion of the trocar 73 into the anvil shaft 104, the trocar tip 75 has a low force profile. Preferably, the trocar tip 75 is tapered at a shallow angle to reduce the force required to bias open the retainer clips 110. For example, the trocar tip 75 is made conical in shape with a taper of 30 degrees or less relative to the trocar axis to facilitate the insertion of the trocar 73 between the retainer clips 110. In a preferred embodiment, the trocar tip 75 has a conical nose 77 at its distal end tapered at 30 degrees and an adjacent conical surface 79 tapered at 9 degrees for biasing open the retainer clips 110 when the trocar 73 is inserted into the anvil shaft 104.

Figure 4:
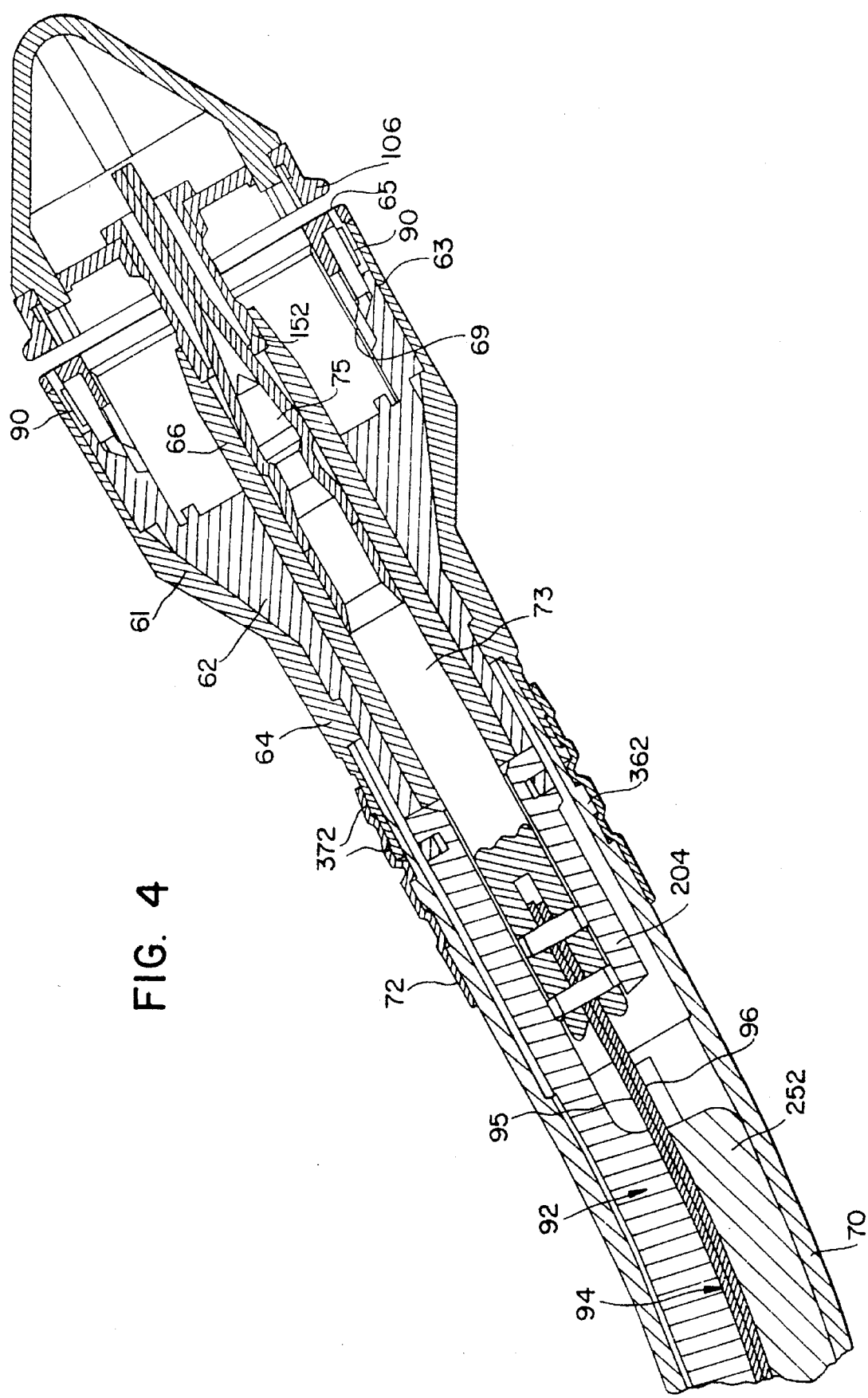
FIG. 4 is an enlarged longitudinal section view of the stapling head assembly illustrating the anvil in a closed position.

With the stapling instrument 50 in its open position (FIG. 2), the retainer clips 110 permit the anvil assembly 100 (FIG. 31) to be attached to or detached from the trocar 73 by pushing or pulling, respectively, on the anvil assembly 100. With the stapling instrument in its closed position (FIG. 4), the trocar 73 is retracted into the central support tube 66 which restricts radial movement of the retainer clips 110 so that the detents 116 are held in place against the trocar tip 75. As a result, the anvil assembly 100 is locked to the trocar 73 so that the anvil 102 can resist the full firing force of the stapling instrument without disengagement of the retainer clips 110 from the trocar tip 75.

As shown in FIG. 34, each retainer clip 110 includes an enlarged head 118 at its distal end which provides one or more lateral projections or shoulders 120 for applying tension to a flange 121 at the distal end of the anvil shaft 104 and to the anvil 102. A pair of internal lands 122 (FIG. 35) on the anvil shaft 104 engage the opposed edges of the retainer clips 110. The lands 122 define a keyway 123 (FIG. 36) within the anvil shaft 104 for aligning the outwardly flared portions 112 of the retainer clips 110 with the elongated slots 114 on opposite sides of the anvil shaft 104.

Referring to FIG. 32, the trocar 73 comprises an elongated cylindrical body 130 having a first conically tapered section 132 terminating in an elongated section 134 of reduced diameter which supports the trocar tip 75 at its distal end. A second conically tapered section 136 terminates at a cylindrical neck 138 of reduced diameter which defines an outwardly projecting shoulder 140 behind the trocar tip 75. The shoulder 140 is engaged by the detents 116 when the trocar tip 75 is inserted between the retainer clips 110.

As shown in FIG. 33, the cylindrical trocar body 130 is offset inwardly at a position adjacent to the first conically tapered section 132 to provide a circumferential lip 142 on the trocar 73. The lip 142 engages the end of the sleeve 105 when the trocar 73 is inserted into the hollow anvil shaft 104. The sleeve 105 has an internally tapered end 124 for receiving the conically tapered section 132 of the trocar body 130. An outer chamfered surface 126 at the proximal end of the sleeve 105 provides a thin circumferential edge 128 for engaging the circumferential lip 142 on the trocar body 130. The trocar 73 has an outer chamfered surface 144 proximally adjacent to the circumferential lip 142. The chamfered surfaces 126 and 144 facilitate the movement of the tissue over the joint between the sleeve 105 and the trocar body 130 as the trocar 73 is retracted into the stapling head assembly 60. Preferably, the circumferential edge 128 of the sleeve 105 has a slightly smaller diameter than the circumferential lip 142 to facilitate the transfer of the tissue from the trocar 73 to the anvil shaft 104.

Referring to FIG. 35, the anvil shaft 104 has a composite structure consisting of the hollow sleeve 105 which is made of metal, e.g., stainless steel, and a thin, hollow cylindrical cover 150 which is made of plastic and secured to the outer surface of the metal sleeve 105. The cylindrical cover 150 includes a raised circumferential section 152 which is slightly larger in diameter than the anvil shaft 104 and the remainder of the cover 150. Alternatively, the anvil shaft 104 can be made as a single piece structure. The raised circumferential section 152 is sized to fit tightly into the distal end of the support tube 66 (FIG. 4) when the trocar 73 and the anvil shaft 104 are retracted into the stapling head assembly 60. The purpose of the circumferential section 152 is to provide precise axial alignment of the anvil 102 with the staple holder 68. Also, a plurality of external circumferentially disposed splines 154 (FIG. 34) extend longitudinally from the raised circumferential section 152 toward the proximal end of the cylindrical cover 150. A plurality of internal circumferentially disposed splines 156 (FIG. 30) is formed on the inside of the support tube 66. When the anvil shaft 104 is retracted into the support tube 66, the external splines 154 are received between the internal splines 156 to provide precise circumferential alignment of the anvil 102 with the staple holder 68. As a result of the precise axial and circumferential alignment, the staple forming grooves 108 on the anvil 102 are accurately aligned with the staple receiving slots 65 in the staple holder 68.

Another purpose of the raised circumferential section 152 is to define a circumferential notch 158 on the anvil shaft 104 which is convenient for purse stringing of the tubular tissue. As shown in FIG. 2, if the tissue is tightly purse stringed to the shaft 104 in the circumferential notch 158 located distally beyond the raised circumferential section 152, the purse stringed tissue cannot easily slip over the raised circumferential section 152. As a result, the purse stringed tissue is confined to the distal region of the anvil shaft 104 beyond the raised circumferential section 152 and the anvil shaft 104 cannot inadvertently slip through the purse stringed tissue.

Figure 30:
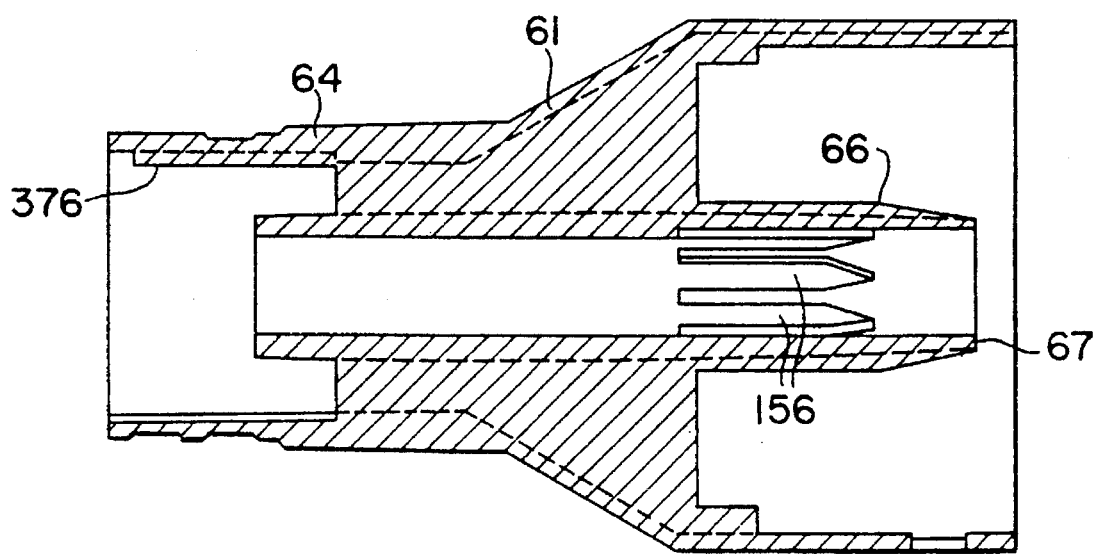
FIG. 30 is a longitudinal section view of a casing for the stapling head assembly.

Preferably, as shown in FIG. 30, the internal splines 156 are spaced proximally away from the distal end of the support tube 66. This placement of the internal splines 156 reduces the tendency of the purse stringed tissue to be pinched between the external splines 154 and the internal splines 156 as the anvil shaft 104 is retracted and prevents the tissue from being pulled into the support tube 66. Also, as shown in FIG. 2, the distal end of the support tube 66 has a planar, annular edge 67 disposed adjacent to the staple holder 68 to push the tissue over the external splines 154 as the anvil shaft 104 is retracted to prevent the tissue from being pulled into the hollow interior of the casing 61. The central support tube 66 provides enhanced visibility as the anvil shaft 104 is retracted into the stapling head assembly 60.

Figure 40:
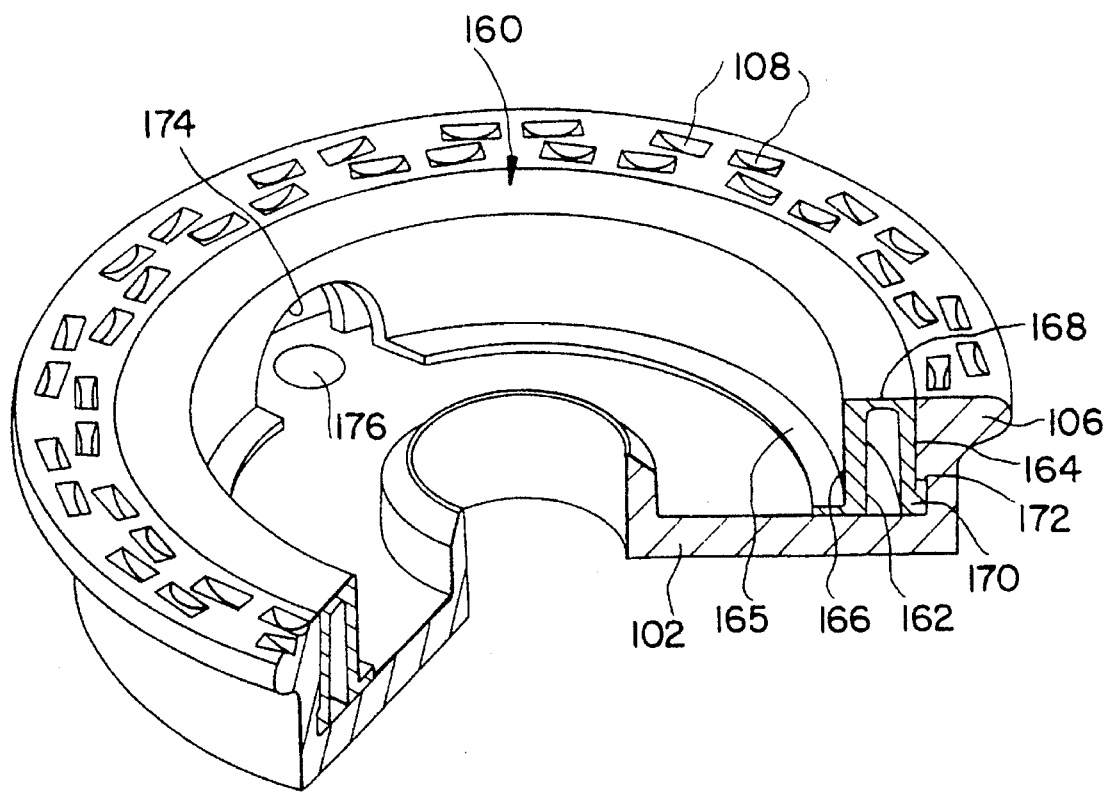
FIG. 40 is an enlarged perspective view, partially cutaway, illustrating the retention of the backup washer by the anvil.

Referring to FIGS. 34 and 40, the anvil assembly 100 includes a backup washer 160 mounted within the anvil 102 to provide a tissue cutting surface against which the purse stringed tissue is severed. The backup washer 160 is annular in configuration and is mounted concentrically inside the annular rim 106 of the anvil 102. An annular groove 162 (FIG. 40) extends inwardly into the washer 160 from its distal end and terminates short of its proximal end. As a result of the groove 162, the washer 160 comprises an outer annular wall 164 and an inner annular wall 166 joined by a thin web 168 at the proximal end of the washer 160. The web 168 provides a backup surface against which the purse stringed tissue is severed by the circular knife 69. An annular flange 165 extends radially inward from the distal end of the inner annular wall 166 and rests on the anvil 102 to strengthen the inner wall 166 of the washer 160.

As shown in FIGS. 34 and 37, the backup washer 160 includes a plurality of detents 170 projecting radially outward at the distal end of the outer annular wall 164. For example, three detents 170 are spaced uniformly about the periphery of the washer 160. An annular recess or groove 172 (FIGS. 15 and 16) is formed distally on the inside of the anvil rim 106 for receiving the detents 170 on the washer 160. The detents 170 are snap fitted into the annular recess 172 to fasten the washer 160 to the anvil 102. The detents 170 and the annular recess 172 provide a frictional force fit which prevents accidental dislodgement of the washer 160 from the anvil 102 during shipment or storage.

The backup washer 160 includes a first pair of semicircular notches 173 (FIG. 37) formed in its outer annular wall 164 which are aligned with a second pair of semicircular notches 174 formed in its inner annular wall 166. The notches 173 and 174 are located at diametrically opposed positions on the washer 160 and are aligned with a pair of holes 176 in the anvil 102. The notches 173 and 174 provide sufficient clearance for receiving the formed ends of a pair of fastening pins 177 used to attach a shroud 178 (FIG. 34) to the anvil 102.

Figure 7:
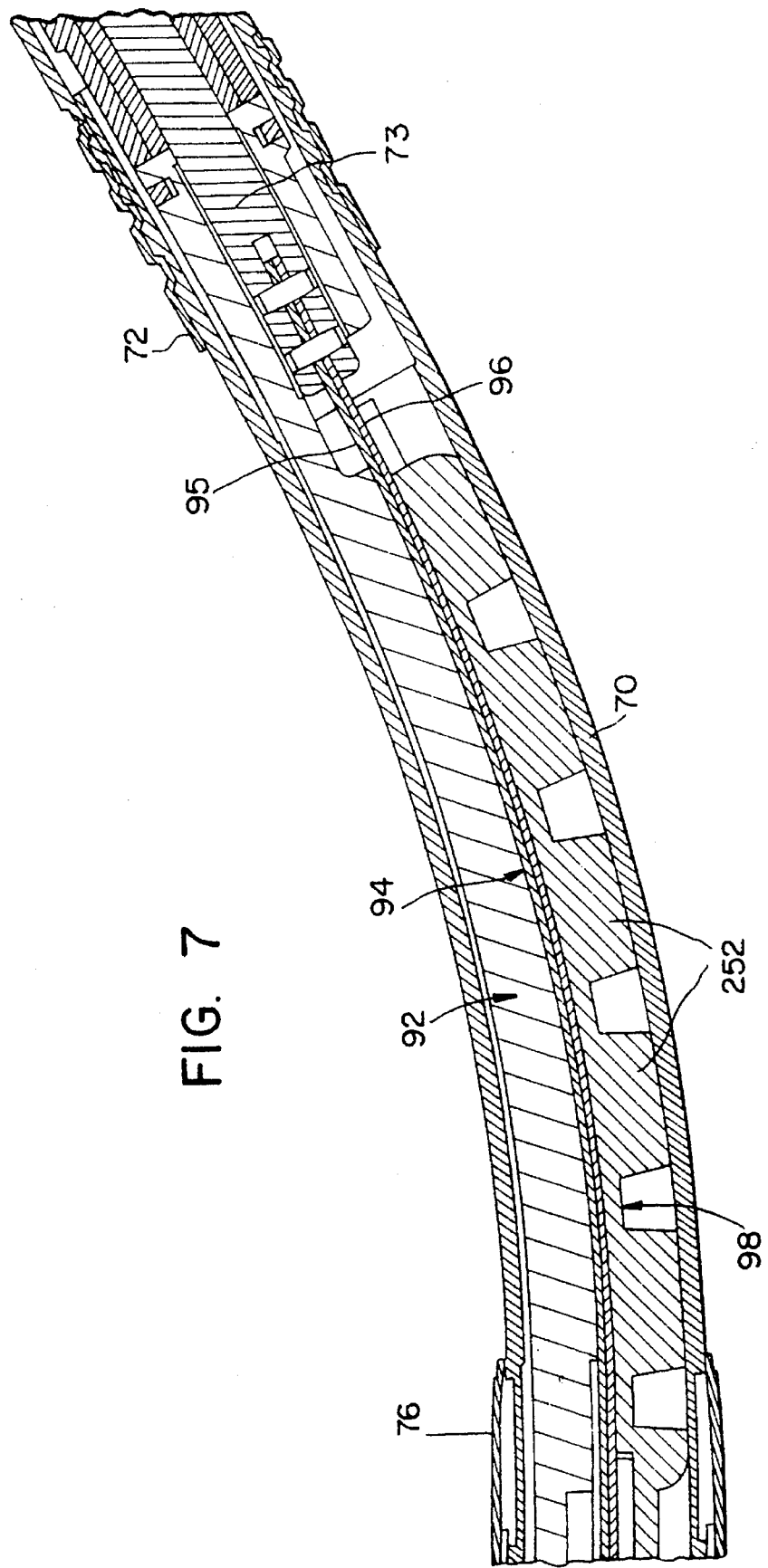
FIG. 7 is an enlarged longitudinal section view illustrating a shaft assembly of the stapling instrument.

Referring to FIG. 7, the support shaft 70 contains a compression member 92 for transmitting the required compressive forces and motion from the actuator handle assembly 80 to operate the staple driver 62 in the stapling head assembly 60. Also, the support shaft 70 contains a tension member 94 consisting of a pair of elongated flexible bands 95 and 96 for transmitting the required tension from the actuator handle assembly 80 to the anvil assembly 100 to resist the compressive forces exerted on the anvil assembly 100. The tension bands 95 and 96 transmit motion from the actuator handle assembly 80 to allow the anvil assembly 100 to be adjusted in position relative to the stapling head assembly 60. An elongated flexible spacer band 98 is contained within the space between the support shaft 70 and the flexible tension bands 95 and 96.

Referring to FIG. 20, the compression member 92 comprises an elongated element, preferably made of plastic material, including a straight proximal portion 200 merging with an intermediate curved portion 202 terminating in a straight sleeve 204 at its distal end. In contrast to the support shaft 70 which is substantially uniform in curvature along its entire length, the intermediate curved portion 202 of the compression member 92 has a varying radius of curvature in the region between the straight proximal portion 200 and the straight sleeve 204 at its distal end. The compression member 92 consists of a material which is flexible in curvature relative to the hollow tubular support shaft 70, for example, a plastic material filled with carbon or glass fibers.

As shown in FIGS. 20 and 21, a proximal extension 206 is defined by an offset 208 on the compression member 92. The proximal extension 206 is provided with an outwardly extending pin 210 to facilitate connection of the compression member 92 to the actuator handle assembly 80. An elongated groove 212 extends from the proximal extension 206 longitudinally along the straight proximal portion 200 and terminates short of the intermediate curved portion 202 of the compression member 92. As shown in FIG. 22, the intermediate curved portion 202 has a solid, non-tubular cross section provided with a raised guide surface or ramp 214 which extends longitudinally along substantially the entire length of the curved portion 202. The ramp 214 provides an integral guide surface on the compression member 92 for engaging and supporting the flexible tension bands 95 and 96 of the tension member 94 contained in the curved support shaft 70.

Figure 26:
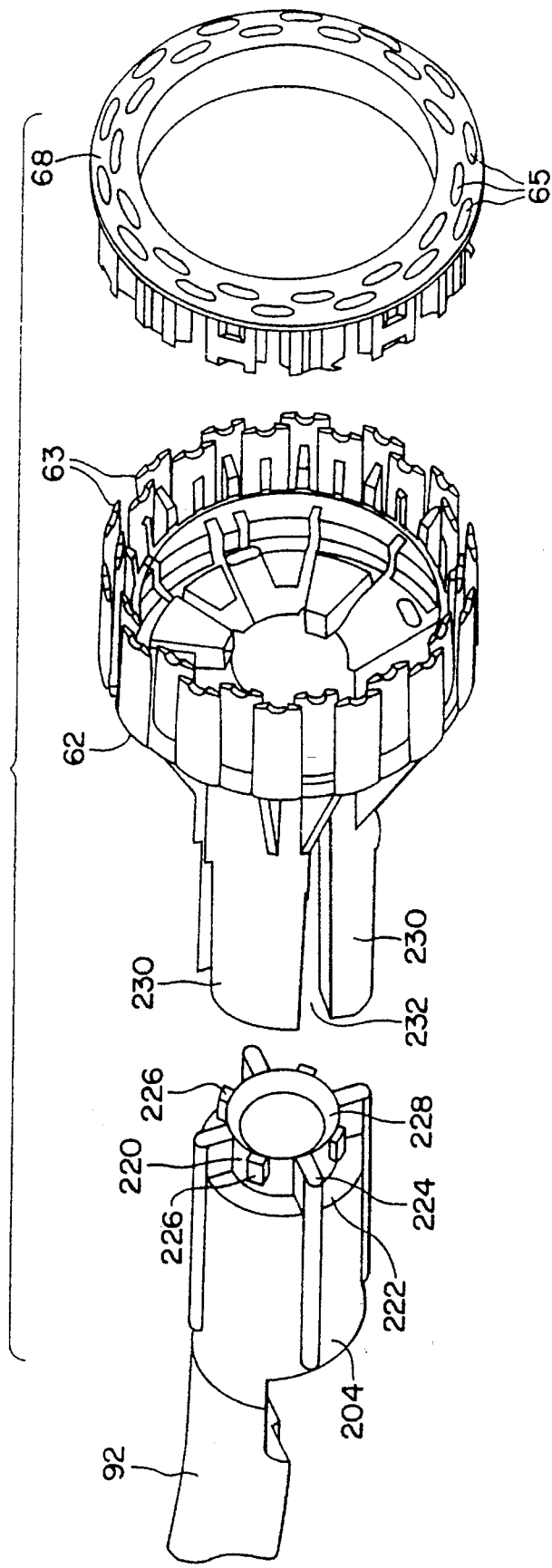
FIG. 26 is an exploded perspective view of the staple holder, staple driver, and distal end of the compression member.

Referring to FIGS. 20 and 26, the sleeve 204 at the distal end of the compression member 92 is adapted to be securely fastened to the staple driver 62 to allow the compression member 92 to advance and retract the staple driver 62 relative to the staple holder 68. The sleeve 204 includes an extension 220 which extends beyond a flange 222 formed at the distal end of the sleeve 204 (FIG. 24). The distal extension 220 is provided with a first set of four radially projecting prongs 224 which are spaced circumferentially apart at equal intervals. Also, the distal extension 220 has a second set of four radially projecting prongs 226 which are spaced circumferentially apart at equal intervals and which are interspersed with the first set of radially projecting prongs 224. As shown in FIG. 23, the first set of prongs 224 extend radially outward by substantially the same distance as flange 222. The second set of prongs 226 is smaller in size compared with the prongs 224 and the prongs 226 extend radially outward by a smaller distance than the prongs 224. Preferably, the distal extension 220 has an inner, chamfered surface 228 (FIG. 24) to facilitate movement of the trocar 73 into the sleeve 204 as the anvil assembly 100 is retracted.

Figure 27:
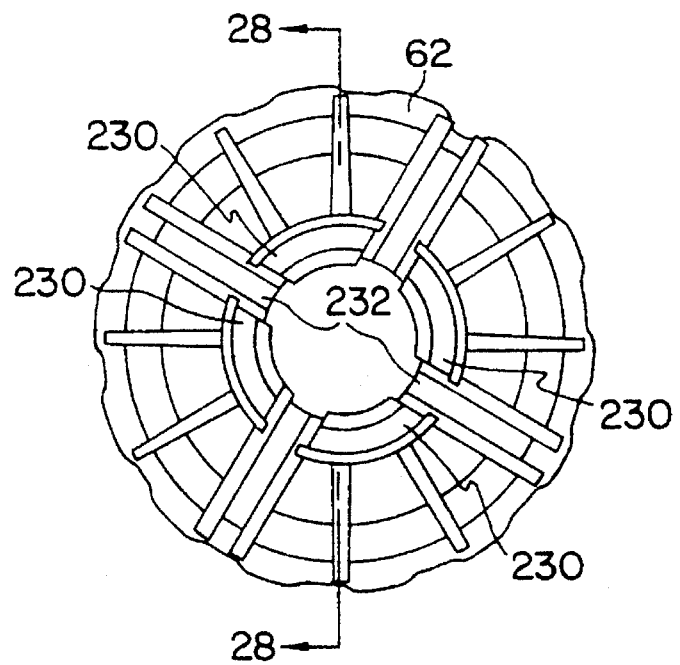
FIG. 27 is an end view of the staple driver.
Figure 28:
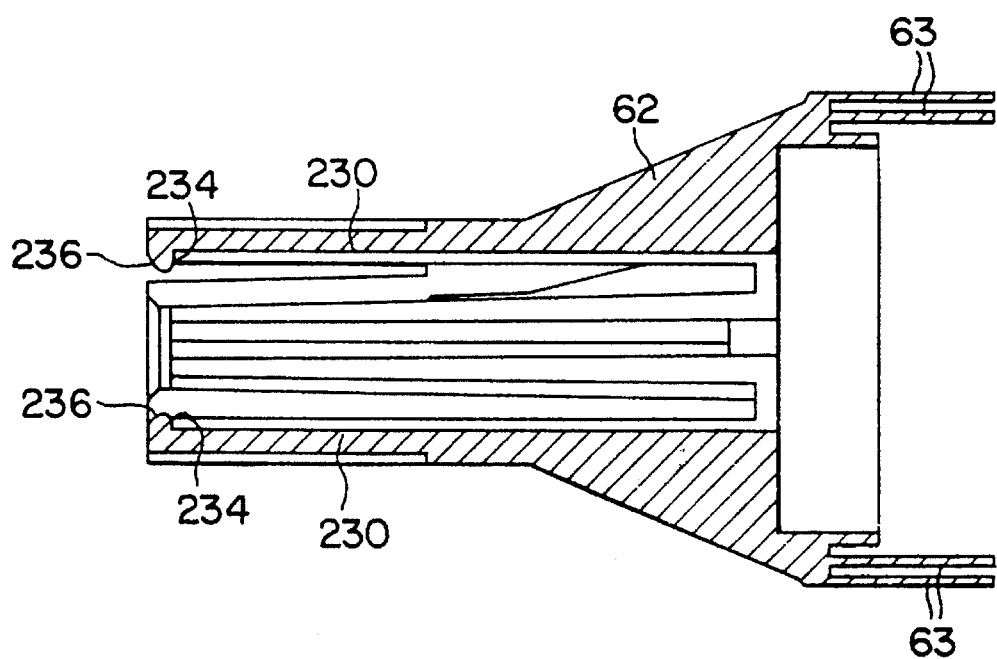
FIG. 28 is a longitudinal section view of the staple driver along line 28—28 of FIG. 27.
Figure 29:
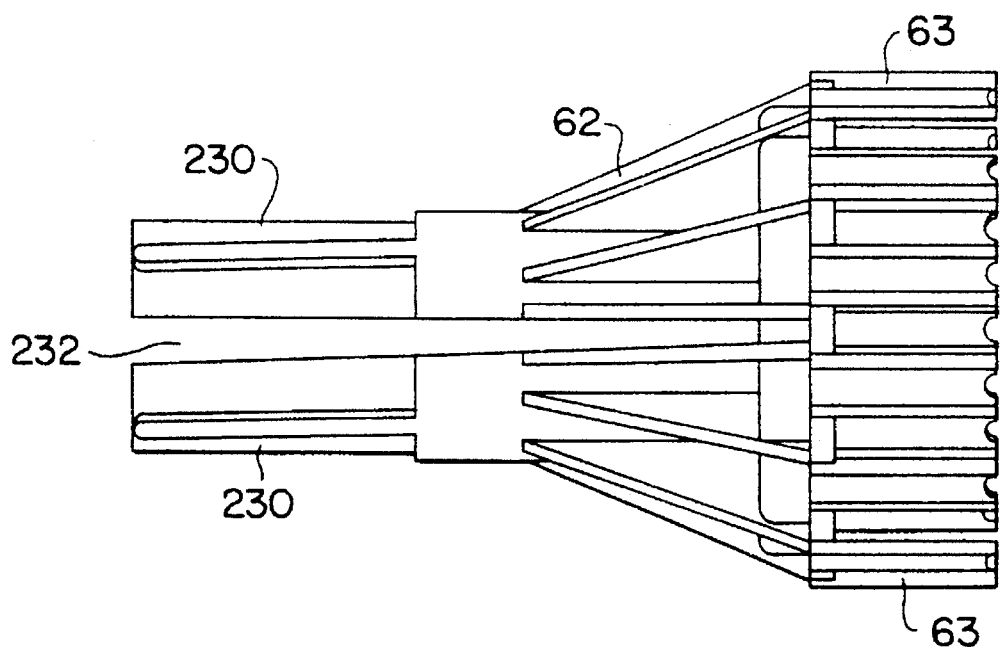
FIG. 29 is a side view of the staple driver.

Referring to FIG. 26, the staple driver 62 includes a set of four elongated, proximally extending locator fingers 230 which are separated by longitudinal slots 232. As shown in FIG. 27, the slots 232 are disposed circumferentially on the staple driver 62 at intervals of 90 degrees. Also, as shown in FIG. 28, each locator finger 230 includes an inwardly projecting detent 234 provided with an inwardly chamfered surface 236 adjacent to the proximal end of the locator finger 230. When the staple driver 62 is attached to the sleeve 204 of the compression member 92, the locator fingers 230 are temporarily flexed apart to allow the detents 234 to move over the prongs 226. The chamfered surfaces 236 facilitate the movement of the detents 234 over the prongs 226. The detents 234 snap into place between the prongs 226 and the flange 222 to fasten the staple driver 62 to the sleeve 204. Also, the large prongs 224 are received in the longitudinal slots 232 to prevent rotation of the staple driver 62 relative to the sleeve 204. The flange 222 transmits compressive forces from the compression member 92 to advance the staple driver 62. The prongs 226 and the detents 234 allow the staple driver 62 to be retracted by the compression member 92.

Referring to FIG. 17, the tension member 94 comprises a pair of flexible metal strips 95 and 96 which enhance the flexibility of the tension member 94 while maintaining its tensile strength. The narrow distal ends of the flexible bands 95 and 96 are connected by a set of pins 240 to the trocar 73. The narrow proximal ends of the flexible bands 95 and 96 are connected by a pin 242 to a control rod 300 contained in the actuator handle assembly 80. The flexible bands 95 and 96 include elongated intermediate sections 245 and 246, respectively, which are substantially wider than the narrow proximal and distal ends of the flexible bands 95 and 96. Because the compression member 92 has an open, non-tubular configuration along substantially its entire length, the tension member 94 is not disposed in or surrounded by the compression member 92. As a result, the elongated intermediate sections 245 and 246 of the flexible bands 95 and 96 are substantially the same in width as the inner diameter of the support shaft 70. This enlarged width minimizes the tendency of the flexible bands 95 and 96 to stretch as tension is transmitted via the tension member 94 from the actuator handle assembly 80 to the annular assembly 100.

As shown in FIGS. 7 and 18, the spacer band 98 comprises an elongated flexible strip 250 which includes a longitudinal row of fins 252 projecting perpendicularly therefrom and engaging the inner surface of the support shaft 70. On top of the spacer band 98, a pair of elongated ridges 254 extend along opposite edges of the flexible strip 250. The ridges 254 engage the intermediate section 246 of the tension band 96 to reduce the sliding friction between the flexible band 96 and the spacer band 98. An elongated groove 256 is formed at the proximal end of the spacer band 98 for receiving the control rod 300 contained in the actuator handle assembly 80.

Figure 19:
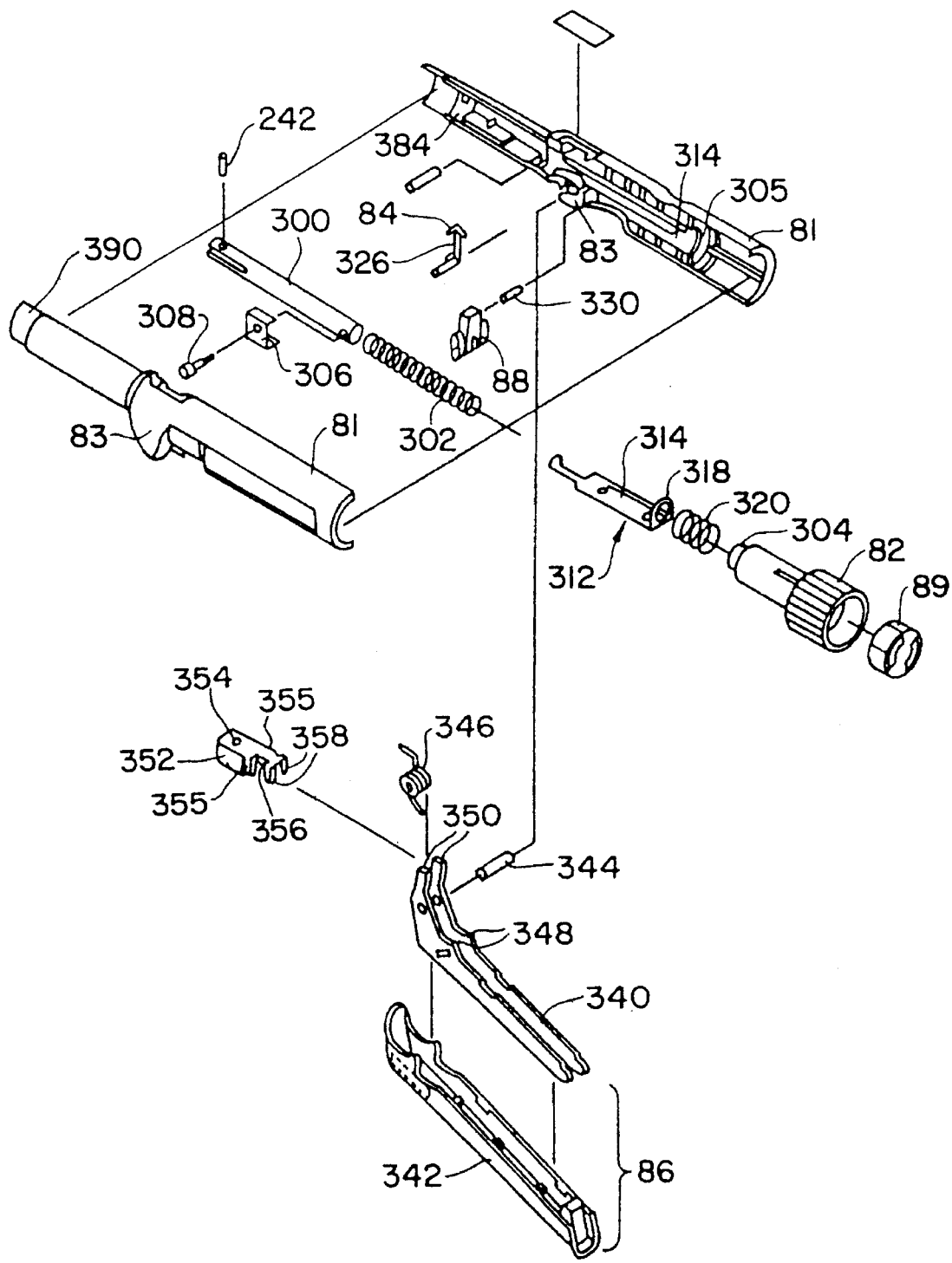
FIG. 19 is an exploded perspective view of the components of the actuator handle assembly.
Figure 25:
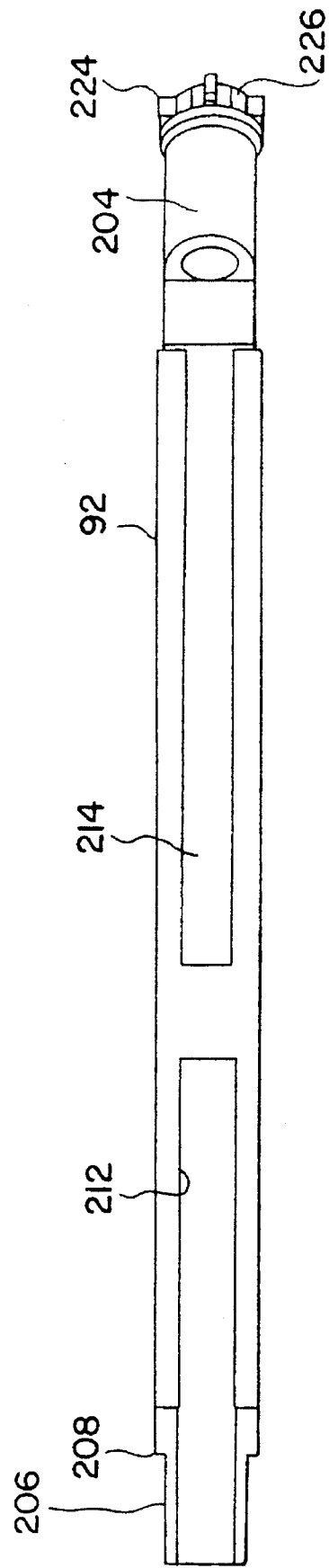
FIG. 25 is a bottom view of the compression member.

Referring to FIG. 19, the actuator handle assembly 80 comprises a pair of elongated handle sections 81 which fit together to form a generally cylindrical handle. Each of the handle sections 81 includes a depending tang 83 on which the staple actuating lever 86 is pivotally mounted. The control rod 300 is contained between the handle sections 81 for longitudinal movement along the actuator handle assembly 80. The adjusting knob 82 is rotatably supported by the proximal ends of the handle sections 81 and is threadably engaged with an elongated threaded shank 302 at the proximal end of the control rod 300. The threaded shank 302 is threadably connected to an internally threaded sleeve 304 at the distal end of the adjusting knob 82. The threaded sleeve 304 is rotatably received in an annular wall 305 formed on each handle section 81. A cylindrical cap 89 is secured within the proximal end of the hollow adjusting knob 82. The distal end of the control rod 300 is slidably received in the elongated groove 212 in the proximal portion 200 of the compression member 92. The control rod 300 is connected at its distal end to the tension member 94 by the pin 242.

As shown in FIG. 19, a U-shaped clip 306 is attached by a screw 308 to an intermediate portion of the control rod 300 located distally of the threaded shank 302. The U-shaped clip 306 and the screw 308 prevent the control rod 300 from rotating about its axis. The U-shaped clip 306 includes an elongated slot 310 (FIG. 2) on each of its opposite sides for receiving the screw 308. The slots 310 permit the U-shaped clip 306 to be adjusted in longitudinal position on the control rod 300 for purposes of calibrating the indicator and safety release mechanism described below.

By rotating the adjusting knob 82 in the counterclockwise direction, as viewed in FIG. 1, the control rod 300 is advanced to move the tension member 94 in the distal direction to open the gap between the anvil assembly 100 and the stapling head assembly 60. A stop 307 (FIG. 8) on one of the handle sections 81 engages the screw 308 to limit the distal movement of the control rod 300. By rotating the adjusting knob 82 in the opposite direction, i.e., clockwise, the control rod 300 is retracted to move the tension member 92 in the proximal direction to close the gap between the anvil assembly 100 and the stapling head assembly 60. A stop 309 on the cap 89 limits the proximal movement of the control rod 300.

The actuator handle assembly 80 includes a safety release bracket 312 which is slidably supported on each of the handle sections 81. The safety release bracket 312 includes an elongated rectangular plate 314 slidably received between a pair of longitudinal ribs 315 and 316 formed on each of the handle sections 81 underneath the threaded shank 302 of the control rod 300. The threaded shank 302 extends through an upstanding flange 318 formed at the proximal end of the rectangular plate 314. A coil spring 320 is interposed between the flange 318 and the annular wall 305 on each handle section 81 to normally bias the flange 318 distally against the rib 315. At the distal end of the safety release bracket 312 is a distally projecting arm 322 which slopes upwardly and terminates at a laterally projecting finger 324 for controlling the movement of the indicator 84.

As shown in FIG. 2, the indicator 84 is located on top of an indicator lever 326 which is pivotally mounted on a pair of pivot pins 328 (one shown) formed on the handle sections 81. The arm 322 extends distally alongside the indicator lever 326 and the finger 324 is located on the distal side of the indicator lever 326. A spring 328 (FIG. 19) is provided to bias the indicator lever 326 distally to locate the indicator 84 in a distal position in the window 85 (FIG. 15).

Figure 8:
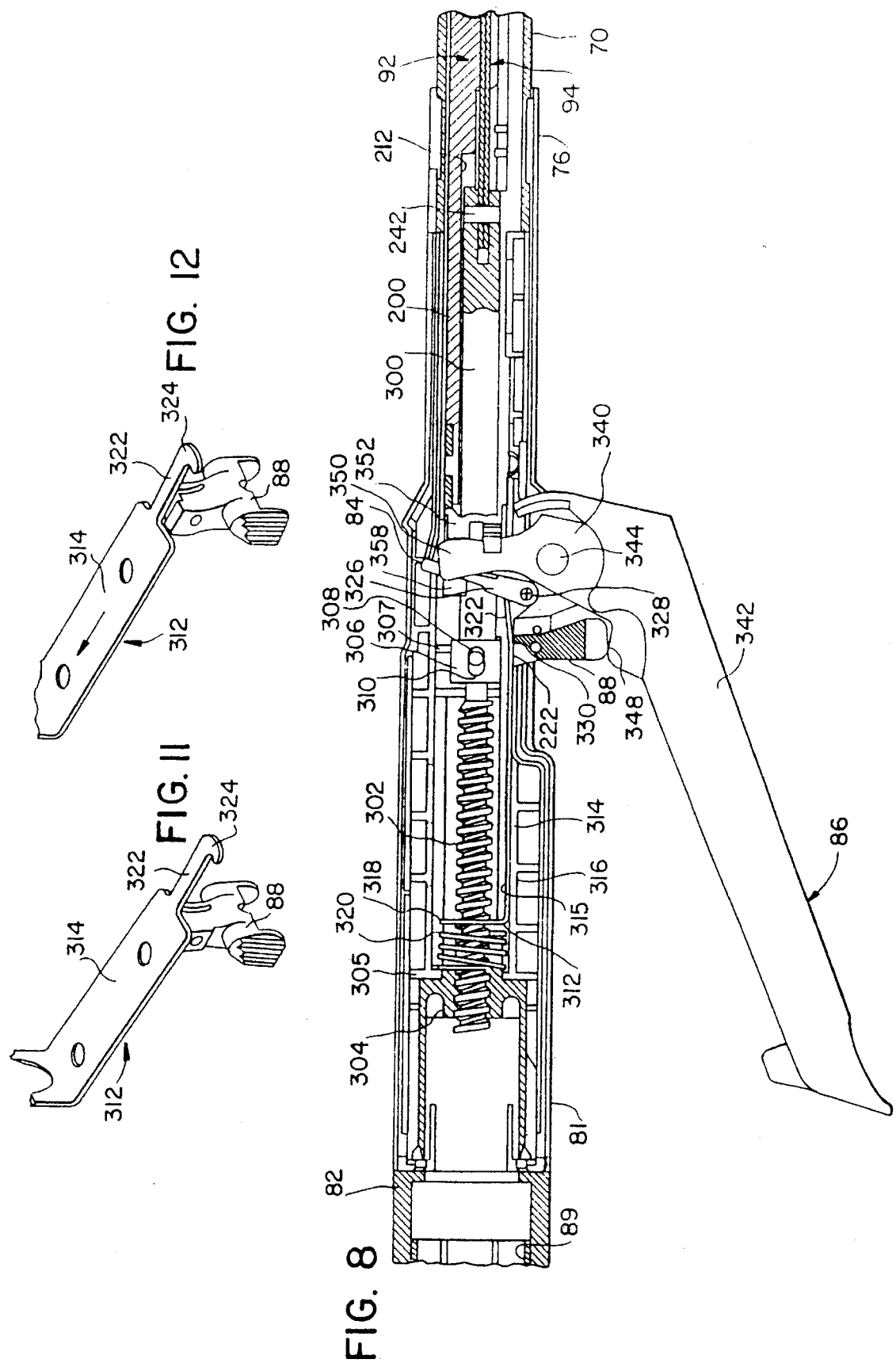
FIG. 8 is a longitudinal, vertical section view of an actuator handle assembly of the stapling instrument of FIG. 1 in a locked position.
Figure 9:
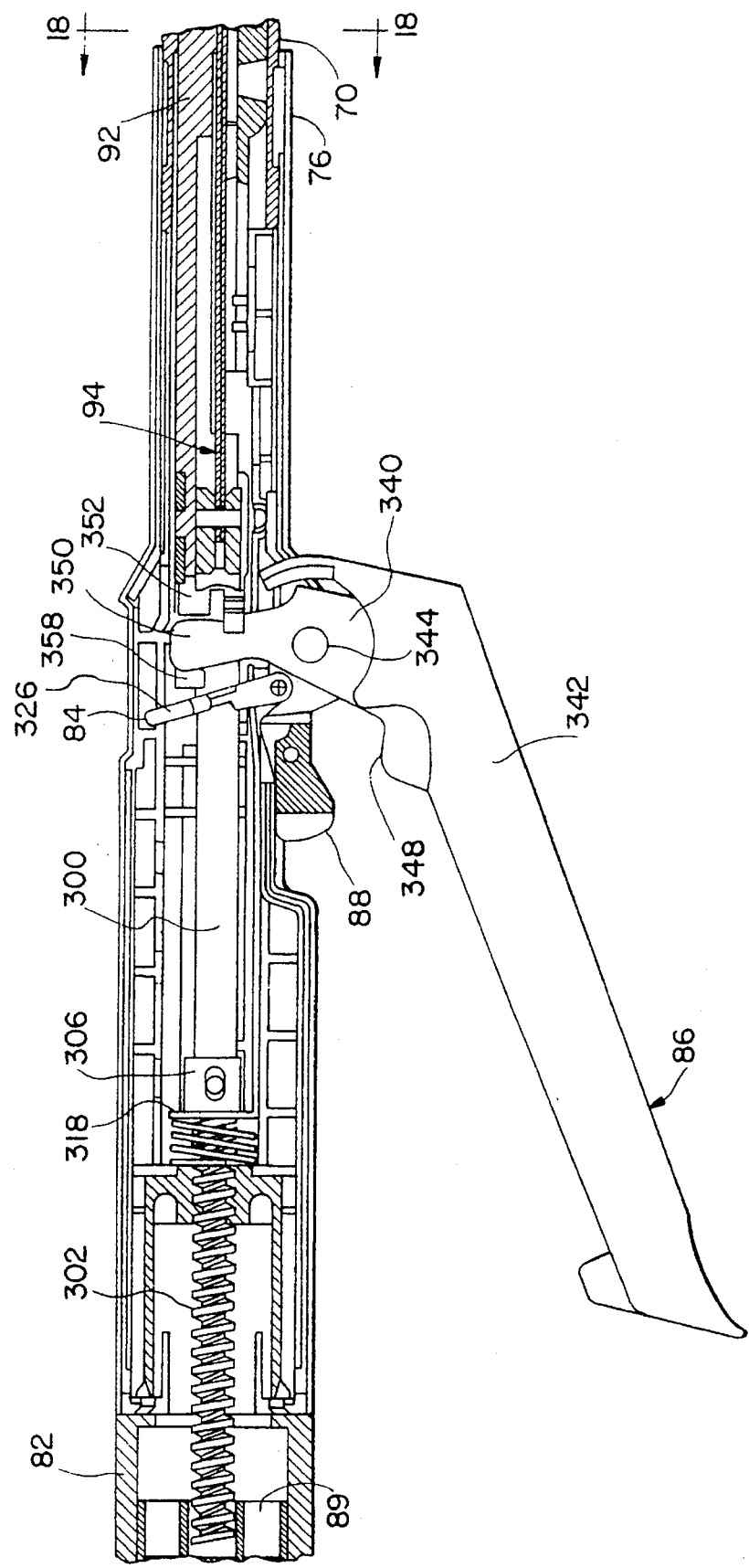
FIG. 9 is a longitudinal, vertical section view of the actuator handle assembly in an unlocked position.
Figure 14:
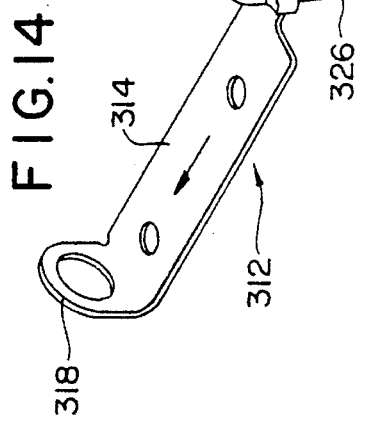
FIG. 14 is a perspective view showing the proximal position of the indicator lever.
Figure 13:
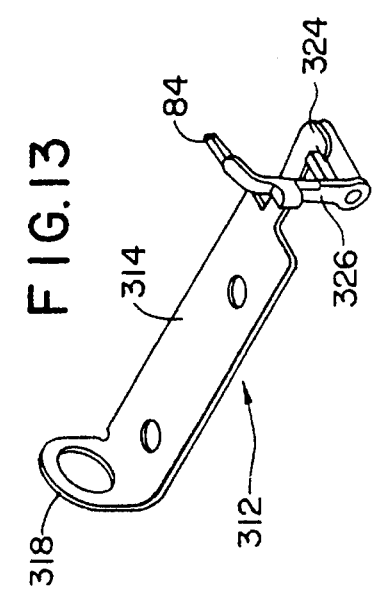
FIG. 13 is a perspective view showing the distal position of an indicator lever actuated by the safety release member.

In FIGS. 2 and 8, the stapling instrument 50 is shown with the anvil assembly 100 fully open and the actuator handle assembly 80 fully advanced. With the anvil assembly 100 fully open, the safety release bracket 312 is biased distally by the coil spring 320 to urge the upstanding flange 318 against the rib 315 with the finger 324 advanced distally and disengaged from the indicator lever 326. When the control rod 300 is retracted, as shown in FIG. 9, the clip 306 on the control rod 300 is moved in a proximal direction to engage the flange 318 and move the safety release bracket 312 in the proximal direction. Initially, as the anvil assembly 100 begins to close, the finger 324 on the safety release bracket 312 remains disengaged from the indicator lever 326 (FIG. 13). When the gap between the anvil assembly 100 and the stapling assembly 60 is adjusted into a predetermined range of the instrument, the finger 324 engages and pivots the indicator lever 326 as shown in FIG. 14, to move the indicator 84 proximally along the scale 87 on the window 85 to provide an indication of the selected staple height to be produced when the stapling instrument is fired.

The safety latch 88 is pivotally mounted beneath the safety release bracket 312 by a pivot pin 330 extending between the handle sections 81. The safety latch 88 includes a ledge 332 which, in its latched position (FIG. 8), is disposed horizontally underneath the safety release bracket 312. If the anvil gap is outside, i.e., above the predetermined range of the stapling instrument, the rectangular plate 314 of the safety release bracket 312 overlaps the ledge 332 on the safety latch 88 and prevents the safety latch 88 from being disengaged from the staple actuating lever 86. On the other hand, when the anvil gap is within the pretermined range, the safety release bracket 312 is retracted and the ledge 332 on the safety latch 88 is disengaged from the rectangular plate 314 of the safety release bracket 312. The safety latch 88 can be pivoted to its unlatched position (FIG. 9) to enable the staple actuating lever 86 to be operated.

As shown in FIG. 19, the staple actuating lever 86 comprises a one-piece folded trigger arm 340 covered by a plastic shroud 342 and pivotally connected by a pivot pin 344 to the tangs 83 of the handle sections 81. A trigger spring 346 is mounted on the pivot pin 344 and normally biases the staple actuating lever 86 to its inoperative position (FIG. 8). The trigger arm 340 includes a pair of ledges 348 which are engaged by the safety latch 88 in its latched position. The trigger arm also includes a pair of actuator fingers 350 for operating the compression member 92 of the stapling instrument. The trigger arm 340 is coupled to the compression member 92 by a firing clip 352 which fits over the tubular extension 206 and engages the offset 208 at the proximal end of the compression member 92. The firing clip 352 includes a hole 354 for receiving the pin 210 on the tubular extension 206. Also, the firing clip 352 is provided with notches 356 on its opposite sides for receiving the actuating fingers 350 of the trigger arm 340. The firing clip 352 provides for the transmission of both distal and proximal motion from the actuating fingers 352 to the compression member 92. The notches 356 prevent the fingers 350 from spreading and bypassing the arms 355 under load, and from bypassing tangs 358 upon retraction.

Figure 41:
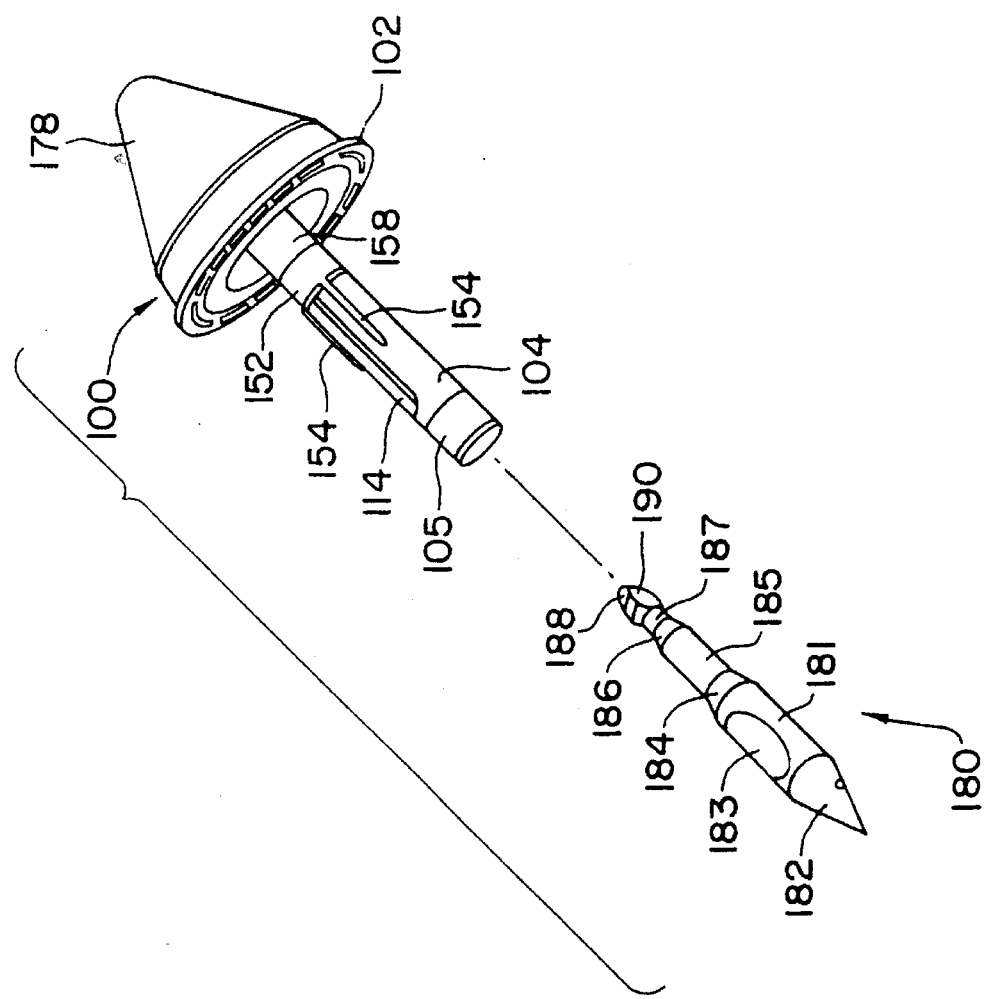
FIG. 41 is a perspective view illustrating a detachable trocar for use with anvil assembly.

Referring to FIG. 41, a detachable trocar 180 is provided for use with the anvil assembly 100. The detachable trocar 180 comprises an elongated, generally cylindrical body 181 having a conically shaped trocar tip 182 at its proximal end. A pair of concave indentations 183 are formed on opposite sides of the cylindrical body 181 which provide convenient finger grips to facilitate the handling of the trocar 180. The cylindrical body 181 has a first conically tapered section 184 terminating in an elongated section 185 of reduced diameter followed by a second conically tapered section 186 terminating at a narrow cylindrical neck 187. An enlarged head 188 is provided at the distal end of the cylindrical neck 187. The head 188 includes a pair of proximal shoulders 189 for engaging the detents 116 of the retainer clips 110 when the head 188 of the trocar 180 is inserted therebetween. The head 188 has a pair of flat, opposed sides 190 displaced circumferentially by 90 degrees relative to the concave finger grips 183 on the trocar body 181.

As shown in FIG. 42, with the detachable trocar 180 inserted into the hollow anvil shaft 104, the sleeve 105 at the proximal end of the anvil shaft 104 engages the conically tapered surface 184 on the trocar 180. In the high force position of the trocar 180 with the flat sides 190 oriented vertically, as shown in FIG. 42, the head 188 is captured by the detents 116 on the retainer clips 110 which engage the shoulders 189 to retain the trocar 180 within the anvil shaft 104. To release the trocar 180 from the anvil shaft 104, the trocar body 181 is rotated by 90 degrees to the low force position shown in FIG. 43 to align the flat sides 190 of the head 188 with the detents 116 on the retainer clips 110. When the trocar 180 is withdrawn from the anvil shaft 104, the flat sides 190 aligned with the detents 116 permit the trocar 180 to be disengaged from the retainer clips 110 with a reduced force in comparison with the force required to withdraw the trocar 180 with the flat sides 190 of the head 188 oriented perpendicularly to the detents 116. Also, when oriented in its low force position, the trocar 180 can be inserted into the anvil shaft 104 and engaged with the retainer clips 110 with a reduced force, e.g., by using an endoscopic grasper.

Referring to 16, the support shaft 70 is offset inwardly at its distal end to provide a tubular extension 360 of reduced diameter having a raised annular collar 362 which defines an adjacent annular groove 364 on the tubular extension 360. Similarly, the tubular connector 62 of the casing 61 includes a proximally extending sleeve 370 with one or more raised annular collars 372 separated by adjacent annular grooves 374. The sleeve 370 is slightly larger in diameter to slidably receive the tubular extension 360 therein. The extension 360 includes a longitudinal slot 366 which provides a keyway for receiving a longitudinal spline or key 376 (FIG. 30) formed internally on the tubular sleeve 370 to circumferentially align the casing 61 with the support shaft 70. The purpose of the annular collars 362 and 372 and the annular grooves 364 and 374 is to provide a series of alternating ridges and depressions adjacent to the point of connection between the tubular casing 61 and the support shaft 70 over which the ferrule 72 is deformed to provide a rigid, non-slip connection between the casing 61 and the support shaft 70.

To facilitate connection of the support shaft 70 to the actuator handle assembly 80, the proximal end of the support shaft 70 is offset to define a tubular extension 380 which is reduced in diameter and is provided with an annular flange 382 at its proximal end. The annular flange 382 is received in an internal annular recess 384 (FIG. 19) on each handle section 81. A pair of guide posts 386 (one shown in FIG. 19) is formed on the handle sections 81 at diametrically opposed positions within the annular recess 384. The guide posts 386 are received in a pair of holes 388 (FIG. 16) formed at diametrically opposed positions on the collar 382. Each handle section 81 includes a semicylindrical sleeve 390 at its distal end for receiving the tubular extension 380 at the proximal end of the shaft 70. The ferrule 76 (FIG. 1) overlaps the point of connection between the support shaft 70 and the actuator handle assembly 80 and is deformed radially inward to provide a rigid connection between the support shaft 70 and the actuator handle assembly 80.

The surgical stapling instrument 50 can be used to perform an intraluminal anastomosis in which two sections of tissue are attached together by an array of staples. By way of example, a procedure for joining a pair of hollow organ sections end to end with a plurality of surgical staples arranged in a circular array around a hollow lumen between the organ sections is described. In preparation for the anastomosis, purse string sutures are placed in the hollow organs to be anastomosed. For example, as shown in FIG. 2, two tubular tissue sections 52 and 54 are prepared by threading purse string sutures 56 and 58, respectively, into the tissue in purse string fashion adjacent to the open ends of the tubular tissue sections 52 and 54.

If the surgical procedure is performed using a double purse string suturing technique, the stapling instrument 50 is inserted into the first tubular tissue section 52, e.g., by insertion into the anal opening of the patient, with the anvil assembly 100 attached to the stapling head assembly 60 and completely closed. Prior to insertion of the stapling instrument 50 into the patient, the adjusting knob 82 is rotated clockwise to retract the trocar 73 into the support tube 66 and to clamp the anvil 102 against the staple holder 68. The stapling head assembly 60 is positioned adjacent to the purse stringed end of the tubular tissue section 52. Next, the adjusting knob 82 is rotated clockwise to advance the control rod 300 and the tension member 92 until the trocar 73 is fully advanced to move the anvil assembly 100 to its fully open position (FIG. 2). With the trocar 73 fully advanced, the purse stringed end of the tubular tissue section 52 is drawn together about the cylindrical trocar body 130 by pulling and tightening the purse string suture 56. The purse stringed tissue is drawn against the cylindrical trocar body 130 and the purse string suture 56 is tied to hold the tissue against the trocar body 130.

The anvil assembly 100 is inserted into the purse stringed end of the tubular tissue section 54 and the tissue is drawn together about the anvil shaft 104 by pulling and tightening the purse string suture 58. Preferably, the purse stringed tissue is pulled against the anvil shaft 104 in the tying notch 158 distally adjacent to the raised circumferential section 152 on the anvil shaft 104 and the purse stringed suture 58 is tied together. If desired, the anvil assembly 100 may be detached from the trocar 73 to facilitate the insertion of the anvil assembly 100 into the tubular tissue section 54. After the purse stringed end of the tubular tissue section 54 is tied against the anvil shaft 104 by the purse string suture 58, the anvil assembly 100 is re-attached to the trocar 73.

After the purse stringed ends of the tubular tissue sections 52 and 54 are tied, the adjusting knob 82 is rotated clockwise to retract the trocar 73 into the support tube 66 to move the anvil 102 toward the staple holder 68. As the trocar 73 is retracted, the trocar body 130 slides through the purse stringed end of the tissue section 52 in the proximal direction to pull the anvil shaft 104 through the purse stringed tissue into the support tube 66. The chamfered surfaces 126 and 144 (FIG. 33) facilitate the movement of the transition point between the trocar body 130 and the sleeve 105 through the purse stringed tissue. As described above, the circumferential edge 128 of the sleeve 105 is slightly smaller in diameter than the circumferential lip 142 on the trocar body 130 to allow the purse stringed tissue to easily move from the chamfered surface 144 to the chamfered surface 126 as the trocar 73 is retracted. When the anvil shaft 104 enters the support tube 66, the external splines 154 (FIG. 34) on the anvil shaft 104 are received and guided between the internal splines 156 (FIG. 30) of the support tube 66 to circumferentially align the anvil 102 with the staple holder 68. The annular edge 67 of the support tube 66 pushes the purse stringed tissue over the transition between the trocar 73 and the anvil shaft 104 and over the external splines 154. Also, the raised circumferential section 152 is tightly received by the support tube 66 to align the anvil 102 axially with the staple holder 68. As a result of this circumferential and axial alignment, the staple forming grooves 108 (FIG. 40) on the anvil 102 are precisely aligned with the staple receiving slots 65 (FIG. 26) of the staple holder 68.

Figure 10:
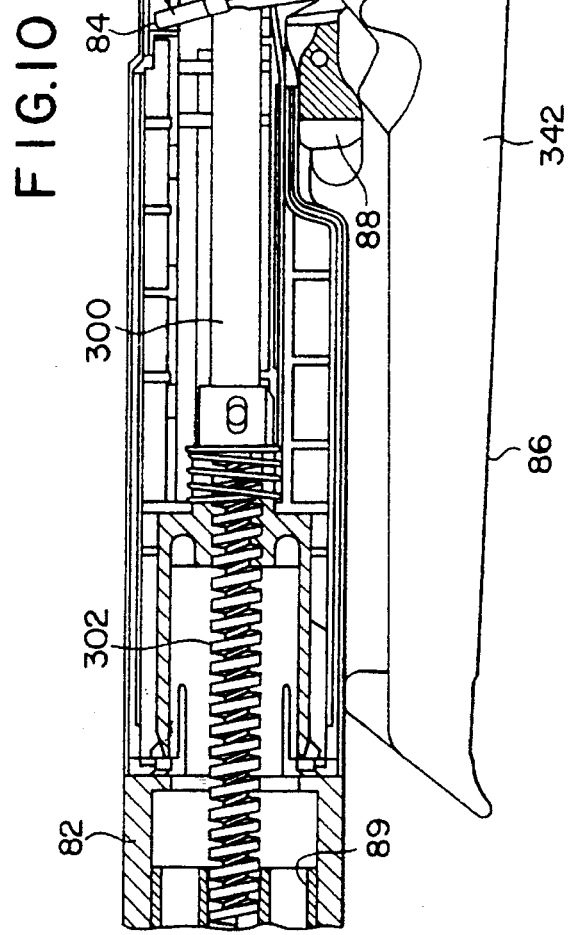
FIG. 10 is a longitudinal, vertical section view of the actuator handle assembly in a fired position.

When the gap between the anvil 102 and the staple holder 68 is set to produce a desired staple height within the operating range of the stapling instrument 50, the safety latch 88 is pivoted clockwise, as viewed in FIG. 9, to disengage the staple actuating lever 86. The stapling instrument 50 is fired by grasping and pivoting the staple actuating lever 86 clockwise, as viewed in FIG. 10, to move the staple actuating lever 86 to its operative position. As a result, the actuator fingers 350 on the trigger arm 340 drive the firing clip 352 in the distal direction to advance the compression member 92 longitudinally along the shaft assembly 70. The compression member 92 advances the staple driver 62 to move the driver fingers 63 distally in the staple receiving slots 65 to engage the staples 90. The compression member 92 transmits the required motion and compressive forces from the trigger arm 340 to the staple driver 62 to drive the staples 90 from the staple holder 68 into the tissue and against the anvil 102. As shown in FIG. 6, each staple 90 is formed into a B-shaped configuration to staple the tissue sections 52 and 54 together. Also, the circular knife 69 is advanced by the staple driver 62 to cut the tissue against the backup washer 160. As shown in FIG. 5, the circular knife 69 splits the backup washer 160 into two annular sections.

After the stapling and cutting of the tissue is completed, the staple actuating lever 86 is biased by the spring 346 to its inoperative position (FIG. 9). The actuator fingers 350 of the trigger arm 340 pivot counterclockwise, as viewed in FIG. 9, to move the firing clip 352 and the compression member 92 in the proximal direction. As a result, the staple driver 62, which is connected by the locator fingers 230 to the compression member 92, and the circular knife 69 are retracted into the stapling head assembly 60. In case of entrapment of staples, tissue or other debris between the staple holder 68 and the driver fingers 63, the retraction of the staple driver 62 frees the stapling head assembly 60 from the tissue before the stapling instrument 50 is withdrawn from the patient. If a high force is required, the staple actuating lever 86 can be returned manually to its inoperative position to retract the staple driver 62.

Next, the stapled tissue between the anvil 102 and the staple holder 68 is released by rotating the adjusting knob 82 counterclockwise to advance the anvil assembly 100 away from the stapling head assembly 60. The anvil 102 is moved through the lumen by manipulating the stapled tissue in a suitable manner to slip the anvil through the stapled lumen. Then, the stapling instrument 50 is withdrawn from the patient leaving behind the stapled lumen between the tubular tissue sections 52 and 54.

Figure 44:
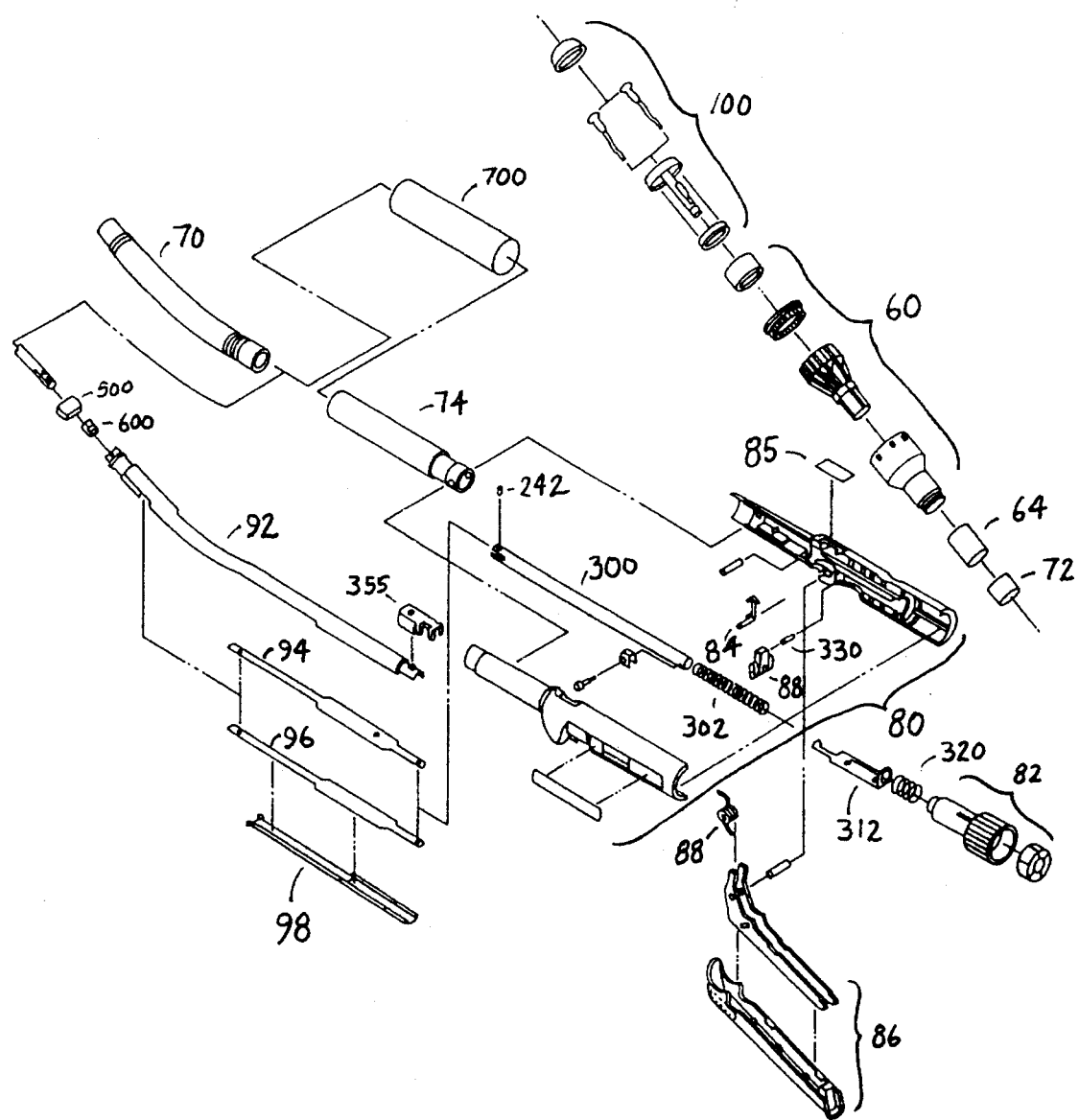
FIG. 44 shows an assembly view of an instrument as in the previous figures, but which incorporates a sealing mechanism more particular to this invention.
Figure 45:
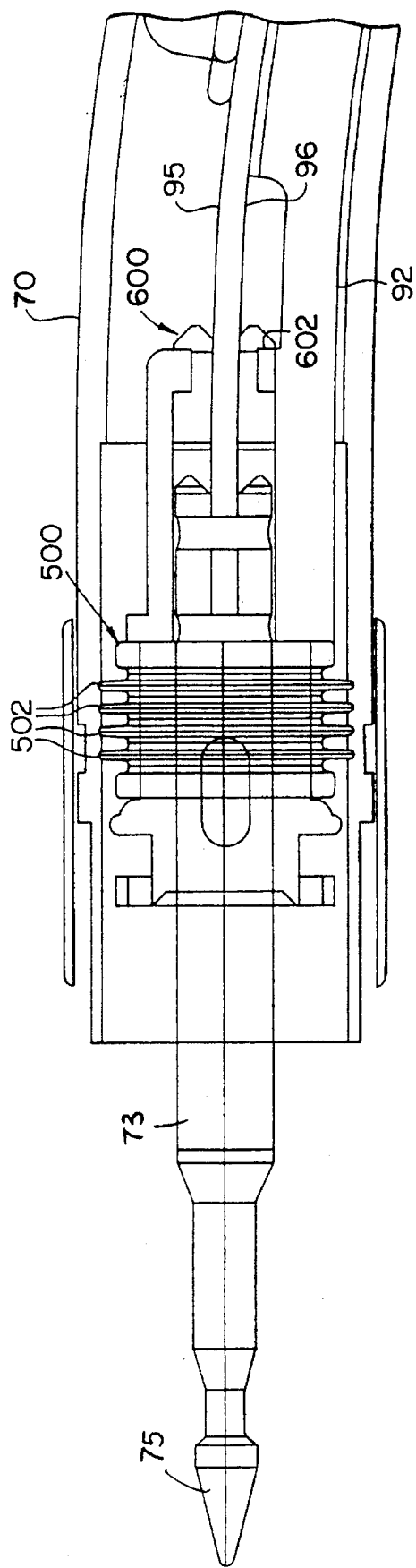
FIG. 45 describes an enlarged cross-sectional view of a portion of the sealing mechanism as seen in FIG. 44 at the stapling head.

Furthermore, as seen in FIGS. 44 and 45, there is described a sealing mechanism which allows the instrument of this invention to be used in an endoscopic procedure. For purposes of interpreting FIGS. 44 and 45, like numerals will be given like characteristics as those elements in FIGS. 1–43. As seen in FIG. 44, taken in conjunction with FIG. 45, there are two necessary internal points of sealing in order to prevent the passage of air through the mechanism. The first sealing point is located outside the circumference of the compression element 92 but inside the circumference of the shaft 70 of the instrument. This sealing is accomplished by the fluted seal 500 as seen in FIGS. 44 and 45. This fluted seal 500 is a rubberized cylindrical mechanism roughly 0.4 inches long which contains four fluted serrating 502 which envelope the entire inner circumference of the shaft 70. The fluted seal prevents the flow of air around the compression element 92 of this mechanism. Further, there can be placed within the serrating 502 of the fluted seal 500 applications of sealing grease, such as lithium or silicone grease, in order to further seal the mechanism about the compression element 92 but within the internal diameter of the shaft 70.

Further, as seen in FIGS. 44 and 45, there is described a tension band seal 600. This seal 600 is better seen in FIG. 45 where it is wrapped about the tension bands 95, 96 of the instrument at the head of the stapler. The tension band seal 600 is similarly an elastomeric rubberized mechanism which may optionally contain silicone grease or other sealing grease within its internal structure. This mechanism 600 encloses the tension bands of the instrument and is held in place at a pair of notch 602, which are diametrically opposed notches about the entire seal 600. Notch 602 mates with compression element 92 about the tension bands 95 and 96. Therefore, in the internal portion of this instrument within shaft 70, there is a nearly complete sealing by the fluted seal 500 and the tension band seal 600. Compressed air is prevented from being forced down the internal portion of the shaft 70 of the stapler.

In order to complete the sealing of this mechanism, there is provided a shrink wrap 700 as better seen in FIG. 44. This shrink wrap 700 fits around the external diameter of shaft 70 and the handle extension. The shrink wrap 700 may optionally contain silicone or lithium grease within its inner circumference or any other seal, which allows the shrink wrap to prevent the flow of air around the shaft or at the handle seams of the mechanism. It has been found that these points of entry may cause leakage within the internal chamber of a trocar. By having a plastic shrink wrap about the shaft, this leakage is prevented. The shrink wrap 700 may be a mechanism which extends the entire length of the shaft 70. However, at least in a preferred embodiment, it has been found that shrink wrap 700 need only be at the base of the shaft toward its proximal end.

Finally, at the magneformed ferrule 76, it has been found that there may also be leakage. Thus, it may be desirable to place an O-ring 76a at the junction of the magneformed ferrule 76 and the shaft 70. This sealing mechanism prevents air from leaking into the internal diameter of the shaft 70, and then through the shaft into the handle portion 80 of the instrument. With this portion of the instrument prevented from leakage, the entire instrument is sealed, and therefore leakage from this instrument is prevented.

This instrument may be placed down a trocar, such as a 33 mm trocar manufactured by Ethicon Endo-Surgery, a division of Ethicon, Inc., Cincinnati, Ohio, a common assignee of this invention. In use, the sealed instrument now prevents leakage of air through its shaft and into the open environment on the proximal side of a trocar. With such sealing, the use of this instrument for endoscopic applications is further enabled, and the benefits of such less invasive surgery are realized.

It is to remember that sealing mechanisms of this device may be useful for other stapling or ligating instruments. For instance, the shrink wrap mechanism as described herein is certainly useful for any shaft of any endoscopic stapling instrument to seal the outer shaft of the instrument. Similarly, the use of the internal seals about any transmission mechanism such as the tension bands or the compression bands as described herein is certainly contemplated by this invention. What is to be remembered, of course, is that sealing takes place due to the blocking of all potential avenues of transmission of air leaking from the mechanism.

The invention in its broader aspects is not limited to the specific details of the preferred embodiments shown and described, and those skilled in the art will recognize that the invention can be practiced with modification within the spirit and scope of the appended claims. Thus, although the invention has been described in the context of a surgical stapling instrument, it is understood that the various aspects of the invention can be applied to surgical instruments which use other types of fasteners such as surgical clips.

We claim:

1. A surgical stapling instrument for applying one or more surgical staples to tissue, comprising:

a stapling head assembly including a staple holder for receiving one or more surgical staples, an anvil for clamping the tissue against said staple holder, and driver means for driving the staples from said staple holder;

an actuator handle assembly for actuating said staple driver;

a shaft assembly with a generally hollow interior and including a support shaft for mounting said stapling head assembly on said actuator handle assembly;

a tension member contained within said support shaft for transmitting tension from said actuator handle assembly to said anvil to resist the forces exerted on said anvil when the staples are formed;

a compression member contained within said support shaft for transmitting a compressive force from said actuator handle assembly to advance said staple driver to drive the staples from said staple holder into the tissue and to form the staples against said anvil; and further containing a shrink wrap plastic seal placed around said shaft assembly, said shrink wrap plastic seal overlapping said shaft assembly and said actuator handle assembly such that said shrink wrap plastic seal prevents the passage of compressed air from the outside to the inside of said shaft assembly for a length of said shaft assembly and for a length of said actuator handle assembly which is overlapped by said shrink wrap plastic seal.

2. The stapling instrument of claim 1 wherein said shaft assembly has an elastomeric seal contained within said hollow interior, said elastomeric seal placed around said tension and compression members.

3. The stapling instrument of claim 1 containing an elastomeric sealing apparatus placed around said tension member and held in place by said compression member.

4. The stapling instrument of claim 1 containing a casing for supporting said stapling head assembly, said casing including a hollow connector;

said shaft assembly including a hollow support shaft for mounting said casing thereon;

a ferrule overlapping said support shaft and said connector;

said ferrule being compressed radially inward over said support shaft and said connector; and an O-ring placed between said ferrule and said shaft assembly.

* * * * *